(12) United States Patent
Funke et al.

(10) Patent No.: US 7,582,262 B2
(45) Date of Patent: Sep. 1, 2009

(54) DISPENSER FOR FLATTENED ARTICLES

(75) Inventors: Tom Funke, Carmel, IN (US); Abner David Joseph, Carmel, IN (US); Peter L. Arnold, Heppenheim (DE); James Meador, Houston, TX (US); Thomas Miller, Houston, TX (US); Randy Edward Yoder, Noblesville, IN (US); Daniel Paul Casler, Fishers, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 678 days.

(21) Appl. No.: 10/871,943

(22) Filed: Jun. 18, 2004

(65) Prior Publication Data

US 2005/0281706 A1 Dec. 22, 2005

(51) Int. Cl.
*B01L 3/00* (2006.01)
(52) U.S. Cl. .......................................................... 422/99
(58) Field of Classification Search ..................... 422/99
See application file for complete search history.

(56) References Cited

U.S. PATENT DOCUMENTS

| | | | |
|---|---|---|---|
| 830,772 | A | 9/1906 | Dunn |
| 892,233 | A | 6/1908 | Erickson |
| 1,042,419 | A | 10/1912 | Farrar |
| 1,236,514 | A | 8/1917 | Weekley |
| 1,598,266 | A | 8/1926 | Davis |
| 2,200,553 | A | 5/1940 | Illmer |
| 2,245,066 | A | 6/1941 | Bouchard |
| 2,265,696 | A | 12/1941 | Mullins |
| 2,626,197 | A | 1/1953 | Kollock |
| 3,100,932 | A | 8/1963 | Pipkin |

(Continued)

FOREIGN PATENT DOCUMENTS

AU 153375 10/2001

(Continued)

OTHER PUBLICATIONS

International Patent Application PCT/EP2007/002852 International Search Report and Written Opinion mailed Oct. 30, 2007.

(Continued)

*Primary Examiner*—Walter D Griffin
*Assistant Examiner*—Bobby Ramdhanie
(74) *Attorney, Agent, or Firm*—Woodard, Emhardt, Moriarty, McNett & Henry LLP

(57) ABSTRACT

A substantially moisture-proof, airtight dispenser for both storing and dispensing several flattened articles such as diagnostic test strips. The inventive dispenser includes a novel pivotable housing that a user need merely grab and squeeze to eject a test strip. Independent movement of the user's fingers to push a button or turn a knob is unnecessary to dispense a strip, which makes the present invention well suited for diabetics suffering from nerve damage in their extremities and other complications resulting from the disease. The invention includes a novel flexible arm member and pusher head that engage and push an article from the dispenser as the two parts of the housing are pivoted together. The articles are dispensed through an exit that is configured with a novel flexible seal that maintains the dispenser substantially airtight. Several inventive seal embodiments and methods of making the same are disclosed.

58 Claims, 25 Drawing Sheets

U.S. PATENT DOCUMENTS

| | | | |
|---|---|---|---|
| 3,159,308 A | 12/1964 | Passavanti | |
| 3,324,538 A | 6/1967 | Christensen | |
| 3,344,951 A | 10/1967 | Gervais | |
| 3,393,948 A | 7/1968 | Brefkr | |
| 3,446,343 A | 5/1969 | Zimmer et al. | |
| 3,728,081 A | 4/1973 | Bidanset | |
| 4,045,102 A | 8/1977 | Austin | |
| 4,088,276 A | 5/1978 | Littleton | |
| 4,142,863 A | 3/1979 | Covington et al. | |
| 4,171,753 A | 10/1979 | Vreede | |
| 4,218,421 A | 8/1980 | Mack et al. | |
| 4,225,410 A | 9/1980 | Pace | |
| 4,328,184 A | 5/1982 | Kondo | |
| 4,428,908 A | 1/1984 | Ashley et al. | |
| 4,440,301 A | 4/1984 | Intengan | |
| 4,471,885 A | 9/1984 | Muccuarone | |
| 4,627,445 A | 12/1986 | Garcia et al. | |
| 4,709,912 A | 12/1987 | Illig et al. | |
| 4,717,018 A | 1/1988 | Sacherer et al. | |
| 4,792,058 A | 12/1988 | Parker | |
| 4,883,197 A | 11/1989 | Sanchez et al. | |
| 4,887,739 A | 12/1989 | Parker | |
| 4,911,344 A | 3/1990 | Kahler | |
| 5,056,682 A | 10/1991 | Meyst et al. | |
| 5,119,969 A | 6/1992 | Haber | |
| 5,271,896 A | 12/1993 | Jakubowicz et al. | |
| 5,510,266 A | 4/1996 | Bonner et al. | |
| 5,525,297 A | 6/1996 | Dinger et al. | |
| 5,575,403 A | 11/1996 | Charlton et al. | |
| 5,615,800 A | 4/1997 | Meyers | |
| 5,632,410 A | 5/1997 | Moulton et al. | |
| 5,649,642 A | 7/1997 | Mabry et al. | |
| 5,660,791 A | 8/1997 | Brenneman et al. | |
| 5,736,103 A | 4/1998 | Pugh | |
| 5,757,666 A | 5/1998 | Schreiber et al. | |
| 5,759,010 A | 6/1998 | Jacobs et al. | |
| 5,797,693 A | 8/1998 | Jaeger | |
| 5,856,195 A | 1/1999 | Charlton et al. | |
| 5,971,941 A | 10/1999 | Simons et al. | |
| 5,988,252 A | 11/1999 | Carroll | |
| 5,989,917 A | 11/1999 | McAleer et al. | |
| 6,027,459 A | 2/2000 | Shain et al. | |
| 6,036,924 A | 3/2000 | Simons et al. | |
| 6,050,449 A | 4/2000 | Kanj | |
| 6,063,039 A | 5/2000 | Cunningham et al. | |
| 6,071,251 A | 6/2000 | Cunningham et al. | |
| 6,071,294 A | 6/2000 | Simons et al. | |
| 6,082,581 A | 7/2000 | Anderson et al. | |
| 6,102,250 A | 8/2000 | Leo | |
| 6,151,110 A | 11/2000 | Markart | |
| 6,283,926 B1 | 9/2001 | Cunningham et al. | |
| 6,302,855 B1 | 10/2001 | Lav et al. | |
| 6,406,922 B2 | 1/2002 | Casterlin et al. | |
| 6,382,460 B1 | 5/2002 | Gonzalez | |
| 6,394,306 B1 | 5/2002 | Pawlo et al. | |
| 6,472,220 B1 | 10/2002 | Simons et al. | |
| 6,491,186 B1 | 12/2002 | Wiggins | |
| 6,508,380 B1 | 1/2003 | Schuckmann | |
| 6,814,844 B2 | 11/2004 | Bhullar et al. | |
| 7,041,206 B2 | 5/2006 | Gephart et al. | |
| 2002/0076349 A1 | 6/2002 | Aitken et al. | |
| 2002/0104849 A1* | 8/2002 | Giruad | 221/270 |
| 2003/0031595 A1 | 2/2003 | Kirchhevel et al. | |
| 2003/0032190 A1 | 2/2003 | Brown et al. | |
| 2003/0089730 A1 | 5/2003 | May et al. | |
| 2003/0116583 A1 | 6/2003 | Pugh | |
| 2003/0133847 A1 | 7/2003 | Hagen et al. | |
| 2003/0175155 A1 | 9/2003 | Charlton | |
| 2003/0185708 A1 | 10/2003 | Otake | |
| 2003/0186446 A1 | 10/2003 | Pugh | |
| 2003/0223906 A1 | 12/2003 | McAllister et al. | |
| 2004/0007585 A1 | 1/2004 | Griffith et al. | |
| 2004/0178216 A1 | 9/2004 | Brickwood et al. | |
| 2005/0281706 A1 | 12/2005 | Funke et al. | |

FOREIGN PATENT DOCUMENTS

| | | |
|---|---|---|
| DE | 42 05 805 | 9/1993 |
| DE | 198 11 622 A1 | 9/1999 |
| EP | 0 645 627 | 3/1995 |
| EP | 0 885 591 | 12/1998 |
| EP | 1152239 | 11/2000 |
| EP | 1147739 | 10/2001 |
| EP | 1360933 | 5/2003 |
| EP | 1362551 | 5/2003 |
| EP | 1321769 | 6/2003 |
| EP | 1 329 395 A1 | 7/2003 |
| EP | 1 347 296 A2 | 9/2003 |
| EP | 1 352 611 | 10/2003 |
| EP | 1 360 935 | 11/2003 |
| GB | 2210603 | 9/1988 |
| JP | 59040145 | 3/1984 |
| JP | 2003/114213 | 4/2003 |
| JP | 2003/215085 | 7/2003 |
| WO | WO 94/10558 | 5/1994 |
| WO | WO 9410558 A1 * | 5/1994 |
| WO | WO 99/44508 | 10/1999 |
| WO | WO 01/64105 | 9/2001 |
| WO | WO 01/78821 | 10/2001 |
| WO | WO 02/08753 | 1/2002 |
| WO | WO 02/18940 | 3/2002 |
| WO | WO 02/49507 | 6/2002 |
| WO | WO 02/055008 | 7/2002 |
| WO | WO 02/078533 | 10/2002 |
| WO | WO 02/085185 | 10/2002 |
| WO | WO 02078533 A2 * | 10/2002 |
| WO | 03/024514 A1 | 3/2003 |
| WO | WO 03/089917 | 4/2003 |
| WO | WO 03/082091 | 10/2003 |
| WO | WO 03/082092 | 10/2003 |
| WO | WO 03/083469 | 10/2003 |
| WO | WO 2004/063747 | 7/2004 |

OTHER PUBLICATIONS

European Patent Application 04 755 540.4 Article 94(3)EPC Communication mailed Jun. 5, 2008.

International Application No. PCT/EP2007/002852 International Search Report and Written Opinion, mailed Sep. 30, 2008.

* cited by examiner

DISPENSER FOR FLATTENED ARTICLES

FIELD OF THE INVENTION

The present invention relates generally to dispensers and more particularly to dispensers for flattened articles such as test strips.

BACKGROUND

Test strips or biosensors for measuring the presence or concentrations of selected analytes in test samples are well known. Typically, several of the test strips are packaged and stored in a disposable vial having a lid that snaps off or unscrews to open. Desiccant material is normally packaged within the vial to maintain the test strips dry. To conduct a test, the user must open the vial and remove a test strip. The strip is then typically inserted into a meter and a fluid sample (normally whole blood) is deposited onto it. The meter then measures the concentration of analyte using photometric or electrochemical methods. When the test is finished, the strip is removed from the meter and discarded.

Test strips are used by diabetics to measure the level of glucose in their blood, which for most diabetics needs to be done three to four times per day, sometimes more frequently. Unfortunately, many diabetics develop complications from having the disease, such as impaired vision, loss of hand-eye coordination, and loss of sensitivity and dexterity of the fingers and toes. These complications of the disease can make opening a test strip vial, extracting a single test strip and manipulating the test strip quite difficult.

Equally undesirably, opening a conventional vial of test strips exposes the strips to moisture in the atmosphere and causes the reagents contained in them to degrade much more quickly than if the vial remained sealed. This exposure significantly reduces shelf life.

SUMMARY OF THE INVENTION

The present invention provides a substantially moisture-proof, airtight dispenser for both storing and dispensing several diagnostic test strips. The inventive dispenser need merely be grabbed by the user and squeezed, thereby ejecting a test strip. Independent movement of the user's fingers to push a button or turn a knob is unnecessary to dispense a strip, which makes the present invention well suited for diabetics suffering from nerve damage in their extremities and other complications resulting from the disease.

In one form thereof, the present invention provides a dispenser for flattened articles. The dispenser includes a housing pivotably connected to a trigger. The housing carries a stack of the articles and the trigger includes an actuation member that engages the uppermost article from the stack and pushes it at least partially out of the dispenser as the trigger and the housing are pivoted together. Either the housing or the trigger defines a receptacle and the other at least partially nests within the receptacle as the housing and the trigger are pivoted together.

In a preferred form, the articles are test strips and the trigger defines the receptacle, such that the housing nests within the trigger as the dispenser is squeezed and a strip is dispensed. The actuation member comprises a novel flexible arm member that flexes upon pivoting movement of the trigger relative to the housing. A pusher head coupled to the arm member is positioned over the stack of articles, and when the trigger and housing are pivoted together, the pusher head is forced downward to frictionally engage the top surface of the uppermost test strip and push it from the dispenser. A spring member biases the trigger and housing apart, so that when the user releases the dispenser after dispensing a strip, it returns to its original or "home" position.

In a further preferred form, the housing and trigger are pivotably connected at bottom portions thereof, such that the nesting occurs mostly at the top of the dispenser. In this configuration, the trigger includes an arcuate inner wall at the top of the dispenser and the housing has a corresponding arcuate outer wall. This allows the housing to nest within the trigger as the two parts are pivoted together. While these two arcuate walls may define somewhat different radii, they at least approximate concentric segments when the trigger and the main housing are pivoted together.

In another preferred form, the inventive dispenser includes a "passive lock" which locks the housing and trigger in the home position and prevents accidental dispensing. The force required to overcome the passive lock is of course greater than the biasing force of the spring, but it is not so great that it prevents the user from squeezing the dispenser and ejecting a test strip.

In another form, the present invention provides a method for forming a substantially airtight seal for a dispenser. In this novel method, a housing is provided which has an opening through which flattened articles are dispensed. A flexible seal is formed, in preferred embodiments by injection molding, with two resilient members having a gap therebetween. After initially forming the seal, it is reconfigured such that the two resilient members are contacting one another and are biased together. The flexible seal is then installed in the opening of the housing.

One advantage of the inventive dispenser is that the diabetic need merely grab it and squeeze it to eject a test strip. The dispenser fits conveniently into the palm of the user and the user-actuable parts that dispense a strip are preferably as large as the dispenser itself. Thus, dispensing a strip with the present invention requires a squeezing action in which all of the fingers essentially work together, thereby avoiding the need for nimble fingers. This is especially advantageous to diabetics who have lost finger sensation and dexterity and thus have trouble manipulating the small dials, caps and sliders present in traditional dispensers.

An additional advantage of the present invention is that the diabetic can place the dispenser on a flat surface while squeezing the trigger to eject a test strip. That is, the configuration of the dispenser enables the user to leverage the dispenser against the flat surface while squeezing it, thus reducing the amount of force required to dispense a test strip.

Another advantage of the present invention is that it maintains the test strips in a substantially moisture-proof environment. Similarly, unlike traditional vials, the present invention prevents the user from touching and thus contaminating the strips before they are used.

A further advantage of the present invention is that the test strips are dispensed one at a time and presented in the same manner each time a test strip is dispensed. Unlike traditional vials, the present invention avoids the need for the user to pick a strip out of the vial. This is especially advantageous to diabetics who have trouble manipulating the small test strips and vials provided in traditional dispensers. Thus, the overall testing time for users is reduced because the user can quickly remove a test strip after dispensing.

Yet another advantage of the present invention is that it uses mostly plastic parts such that it can be mass-produced cost-effectively. The dispenser can therefore be manufactured and sold as a disposable item.

Still another advantage of the present invention is that it provides a substantially airtight seal through which the strips are dispensed. The seal is improved by inverting it or turning it inside out after manufacturing.

Yet another advantage of the present invention is that the substantially airtight seal just noted is "self closing." That is, after a test strip is dispensed through the seal, the resilient members of the seal return to their original positions in which they are biased together. Advantageously, this avoids the problem of users forgetting to close the dispenser, as often happens with traditional vials.

Yet another advantage of certain embodiments of the present invention is that the dispenser can hold the test strip in a position in which the meter insertion end is extended from the dispenser while the user inserts the extended end of the strip into a meter. Thus, the user does not need to touch the test strip to insert it into a test meter, which avoids the user touching and thus contaminating the strips before they are used.

BRIEF DESCRIPTION OF THE DRAWINGS

The above-mentioned and other advantages of the present invention, and the manner of obtaining them, will become more apparent and the invention itself will be better understood by reference to the following description of the embodiments of the invention taken in conjunction with the accompanying drawings, wherein.

Corresponding reference characters indicate corresponding parts throughout the several views.

DESCRIPTION OF THE PREFERRED EMBODIMENTS

For the purposes of promoting an understanding of the principles of the invention, reference will now be made to the specific embodiments illustrated herein and specific language will be used to describe the same. It will nevertheless be understood that no limitation of the scope of the invention is thereby intended. Any alterations and further modifications in the described processes or devices, and any further applications of the principles of the invention as described herein, are contemplated as would normally occur to one skilled in the art to which the invention relates.

Figure 2:
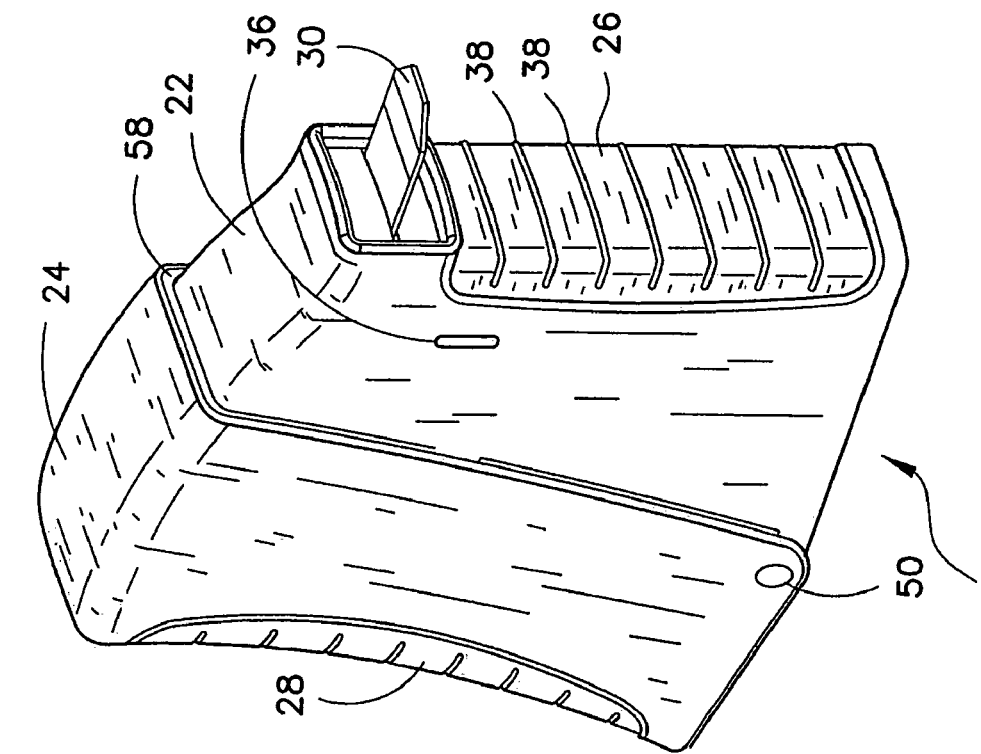
FIGS. 1 and 2 are perspective views of an article dispenser in accordance with the present invention, illustrating the home and dispensed positions of the dispenser.
Figure 1:
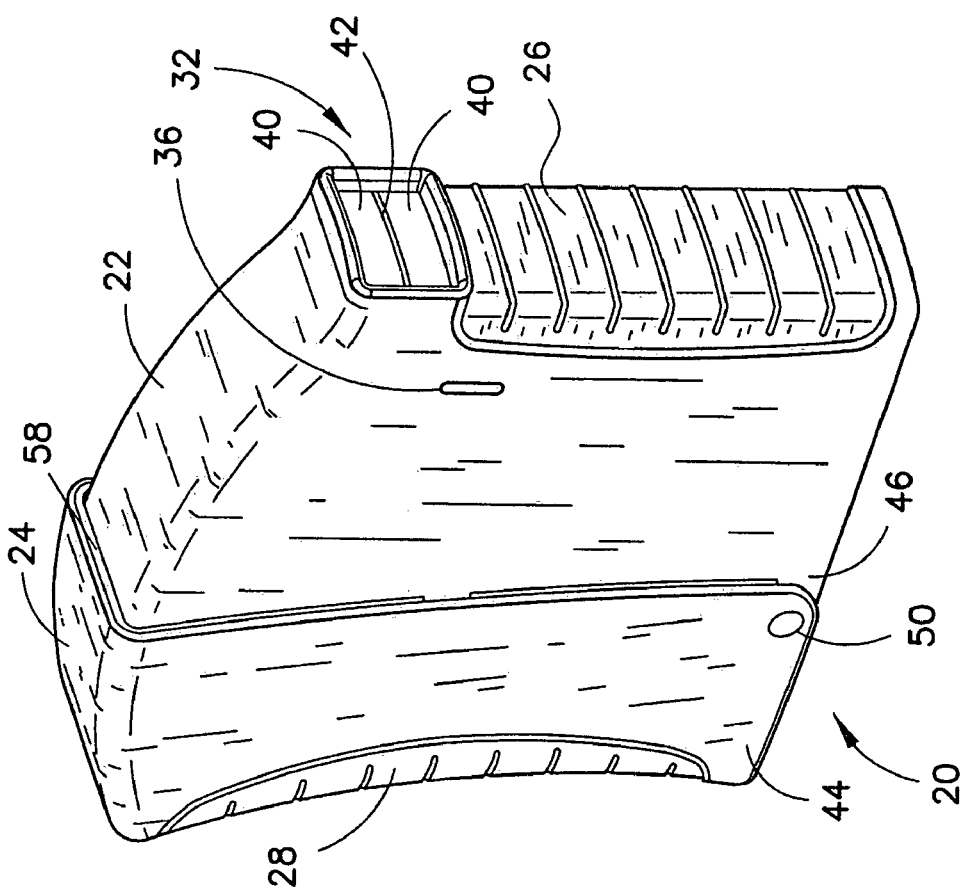
Figure 3:
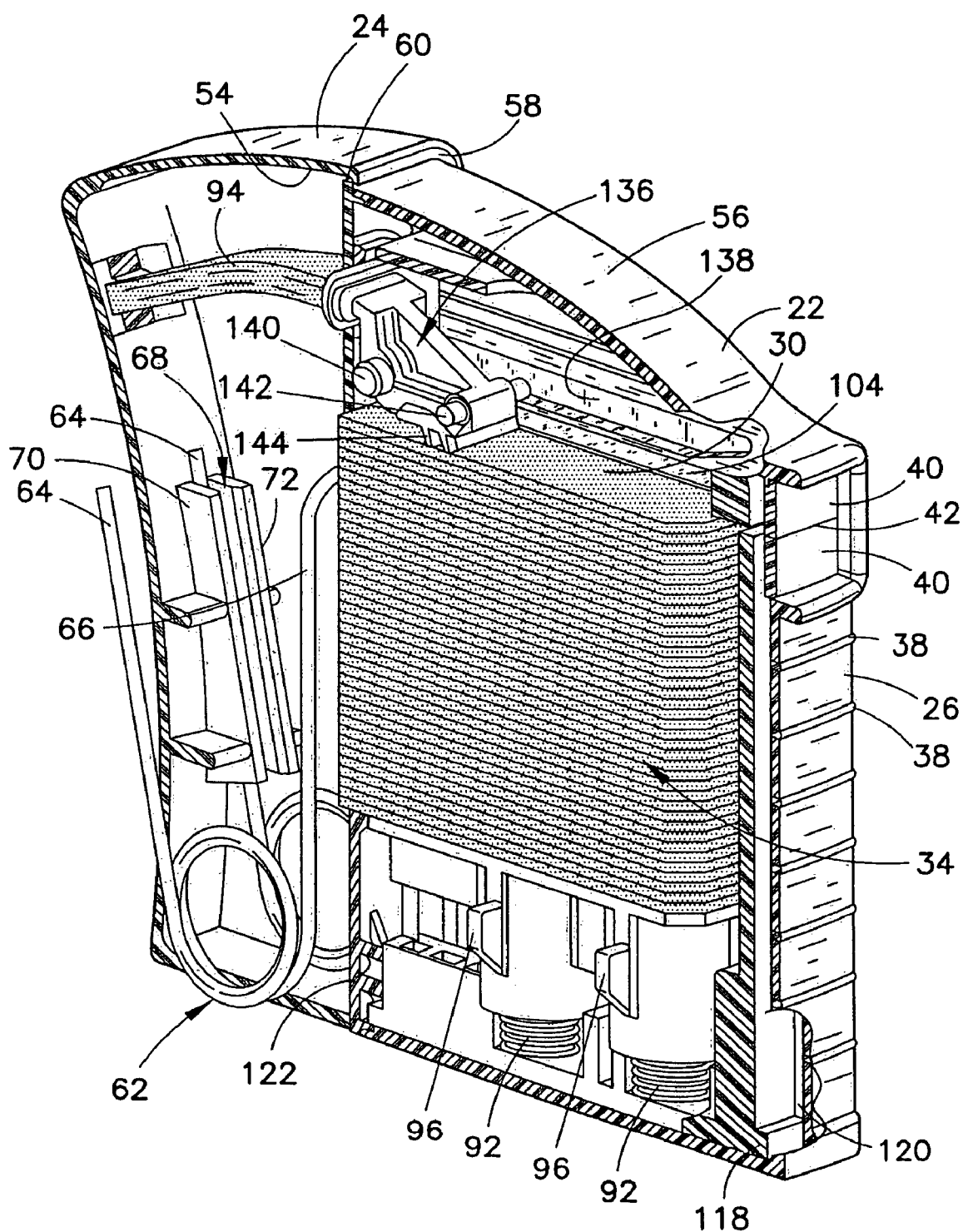
FIG. 3 is a perspective view in partial cross section of the dispenser shown in FIGS. 1 and 2, illustrating the interior components of the dispenser.

Turning now to FIGS. 1 and 2, an article dispenser 20 for dispensing flattened articles such as biosensors or test strips is shown having a main housing 22 pivotably connected to a trigger or rear housing 24. FIG. 1 illustrates a "home" position whereas FIG. 2 illustrates a "dispensed" position for dispenser 20. Dispenser 20 includes front grip section 26 and rear grip section 28, which, when pivoted together as shown in FIG. 2 and explained in detail below, causes an article 30 to be pushed at least partially out of exit 32. In the illustrated embodiment, article 30 is a test strip, e.g., an Accu-Chek® brand glucose test strip that is commercially available from the assignee of the present invention. However, it should be understood that the teachings of the dispenser disclosed herein may be employed for dispensers of other flattened articles. As shown in FIG. 3, main housing 22 carries a stack 34 of test strips 30 to be successively dispensed from dispenser 20, as explained below. Housing 22 includes a window 36 (FIGS. 1 and 2) for viewing the quantity of articles 30 remaining in stack 34. Window 36 may be formed of any number of clear materials, e.g., clear polypropylene.

In the illustrated embodiment, housing 22 and trigger 24 are formed of polypropylene and polystyrene, respectively, but it should be readily appreciated that many other plastics, composites or other materials may be used. Grip section 26 includes protruding ribs 38 that are preferably formed of a thermoplastic elastomer such as Santoprene®, available from Advanced Elastomer Systems, Akron, Ohio. Exit 32 includes flaps 40 that define a lip seal 42. Flaps 40 are also made from Santoprene® and are integrally formed with ribs 38 as illustrated in FIG. 3.

Figure 4:
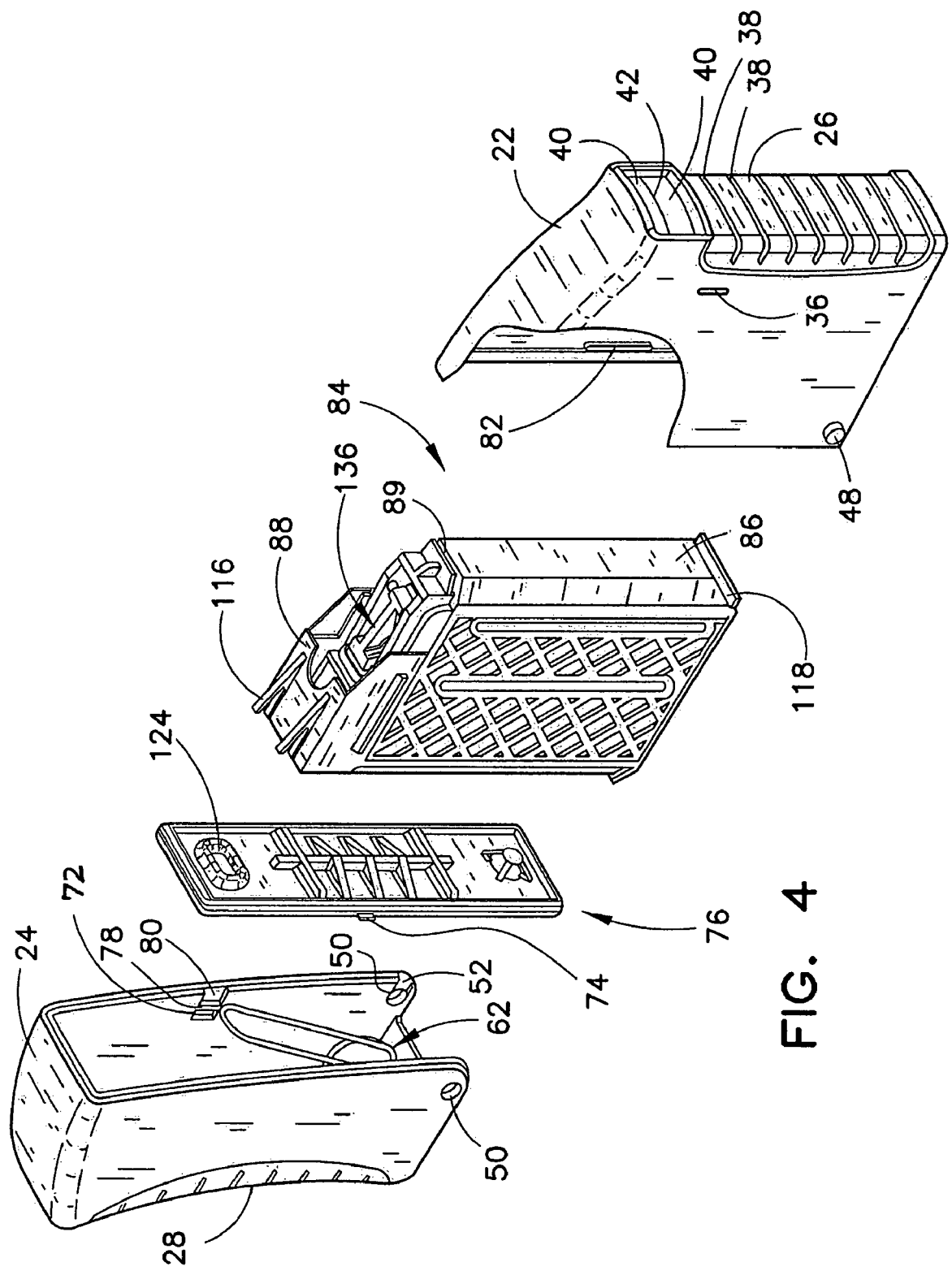
FIG. 4 is an exploded perspective view of the dispenser shown in FIGS. 1 and 2.

With further reference to FIGS. 1 and 2, trigger 24 and housing 22 are pivotably connected at bottom portions 44 and 46, respectively, which results in housing 22 nesting within trigger 24 mainly at the top of dispenser 20. The bottom portions of the trigger and housing do not significantly nest together, which allows cassette 84 (FIG. 4) to be secured to the bottom of housing 22 without interference from trigger 24 when the two are pivoted together during dispensing. As shown in FIG. 4, housing 22 includes cylindrical posts 48 extending laterally therefrom that are rotatably received in corresponding cylindrical openings 50 in trigger 24. The inside surface of trigger 24 is formed with slots 52 that lead to openings 50, which aids assembly of dispenser 20 by allowing posts 48 to slide through slots 52. While the illustrated embodiment includes posts 48 formed on housing 22 and openings 50 on trigger 24, the situation could be reversed. Further, other means for making the pivotal connection between housing 22 and trigger 24, e.g., a hinge, could be substituted for the posts and openings.

As shown in FIGS. 1 and 2, since the pivotal connection is made at bottom portions 44 and 46, most of the movement of trigger 24 and housing 22 relative to one another occurs toward the top of dispenser 20. Trigger 24 has a profile that substantially matches that of housing 22 but is slightly larger, such that the inner surface of trigger 24 defines a receptacle for housing 22. As shown more clearly in FIG. 3, trigger 24 defines an arcuate inner wall 54 that has an arcuate profile similar to that of outer wall 56 defined by housing 22. Thus, when trigger 24 and housing 22 are pivoted toward one another, housing 22 partially nests within trigger 24 while an article 30 is expelled partially from dispenser 20 as shown in FIG. 2. As shown in FIG. 7c, inner wall 54 and outer wall 56 approximate concentric segments when trigger 24 and housing 22 are pivoted together.

Figure 1A:
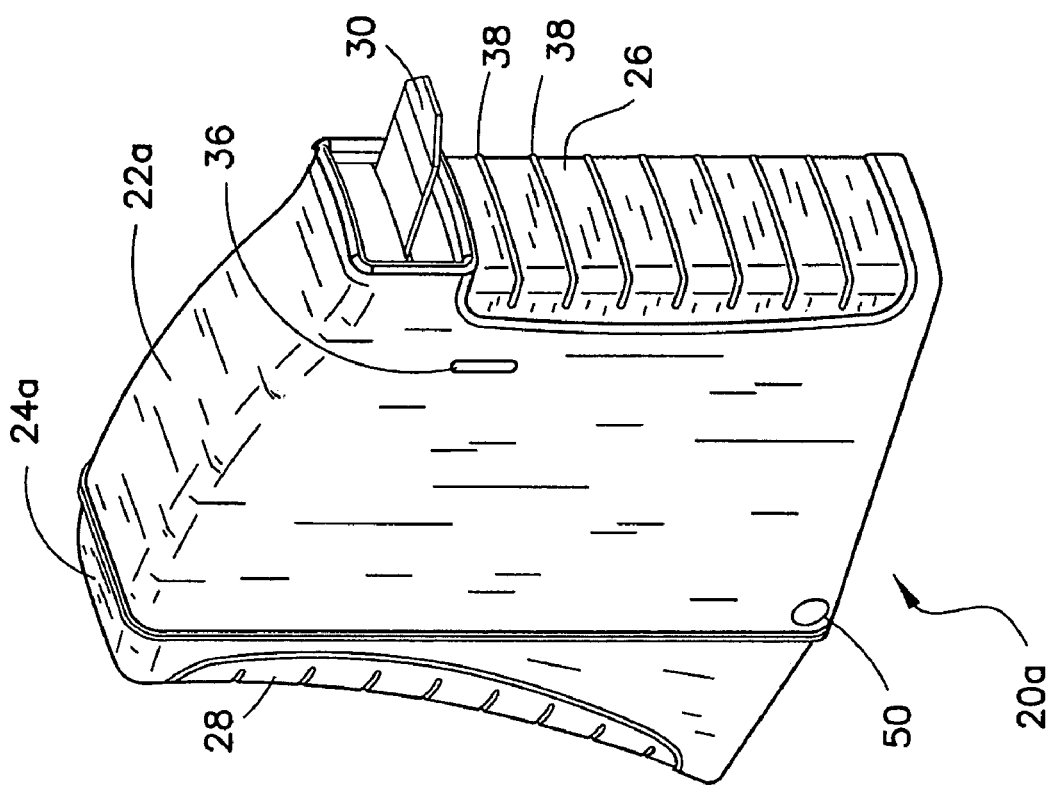
FIGS. 1a and 2a are perspective views of an alternate embodiment of an article dispenser in accordance with the present invention, illustrating the home and dispensed positions of the dispenser.
Figure 2A:
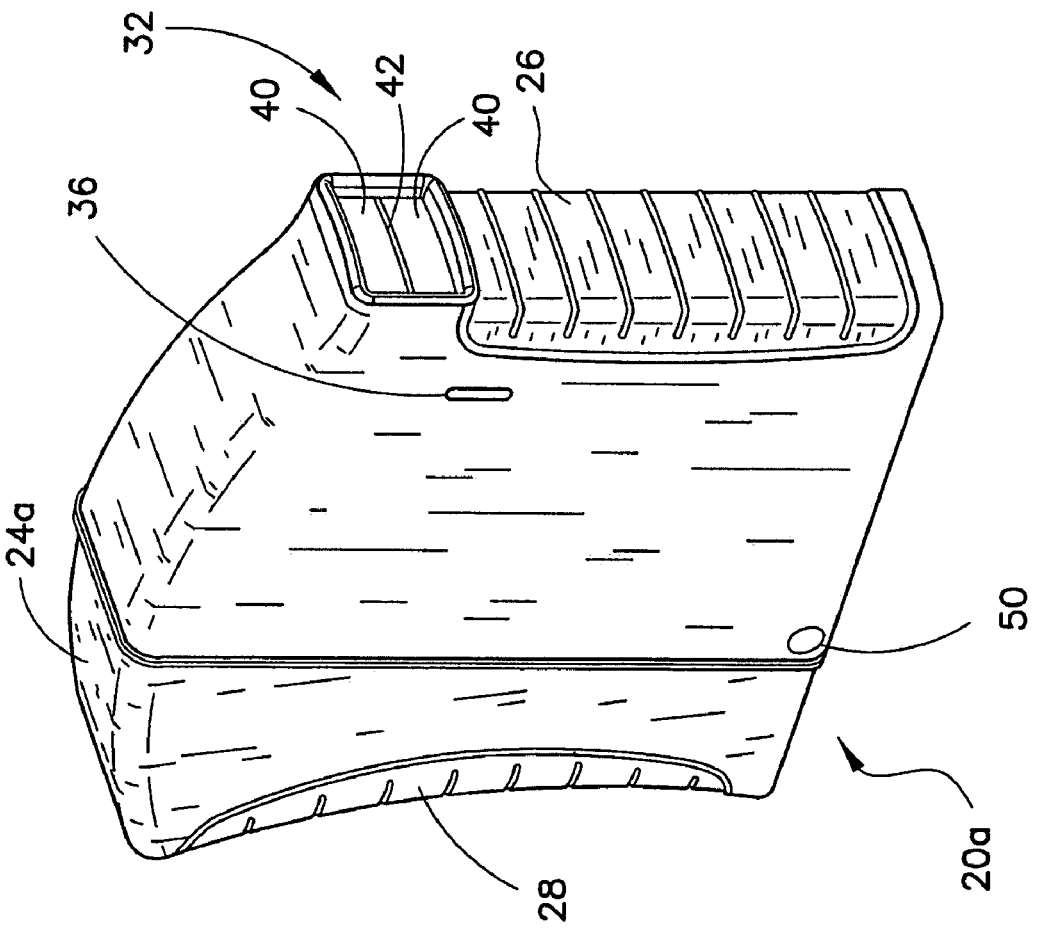

While in the preferred embodiment the trigger forms the receptacle, the inventive pivoting housing principle could be employed if the situation were reversed. As shown in FIGS. 1a and 2a, trigger 24a partially nests within a receptacle defined by main housing 22a as the two parts are pivoted together, and a test strip 30 is expelled partially from container 20a. Other variations of the novel housing of the present invention would be recognized by one of ordinary skill in the art. As noted above, one advantage of this novel pivoting housing is that the actuable parts of the housing that cause a strip to be dispensed can be made as large as the dispenser itself. Thus, dispensing a strip with dispenser 20 or 20a requires only an overall squeeze of the hand, and which does not require individual movement of the fingers. As noted above, this is especially advantageous to diabetics who have lost finger sensation and dexterity and thus have trouble manipulating the small dials, caps and sliders present in prior art dispensers.

As shown in FIG. 3, a torsion spring 62 has upstanding legs 64 and 66 which push against the interior of trigger 24 and housing 22, respectively, biasing the dispenser in the home position shown in FIG. 1. Spring 62 is held in place by means of channels 68 formed by spring retaining plates 70 and 72 formed in trigger 24 and which channels 68 captively hold legs 64. One of ordinary skill in the art would readily recognize many alternative spring mechanisms that could be configured and substituted for the torsion spring 62 of the illustrated embodiment.

Figure 8A:
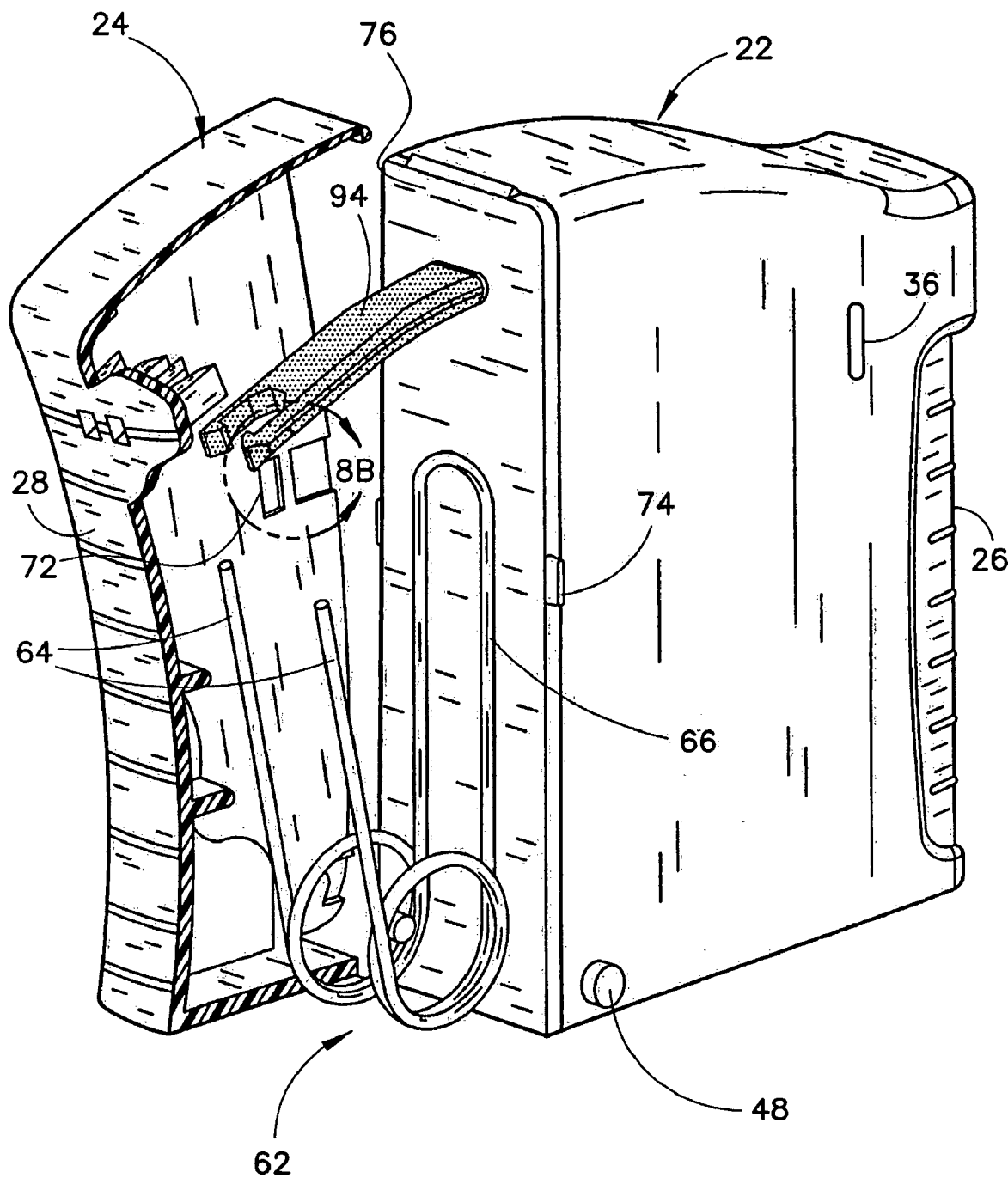
FIG. 8a is an exploded perspective view with portions broken away of the dispenser of FIGS. 1 and 2.
Figure 8B:
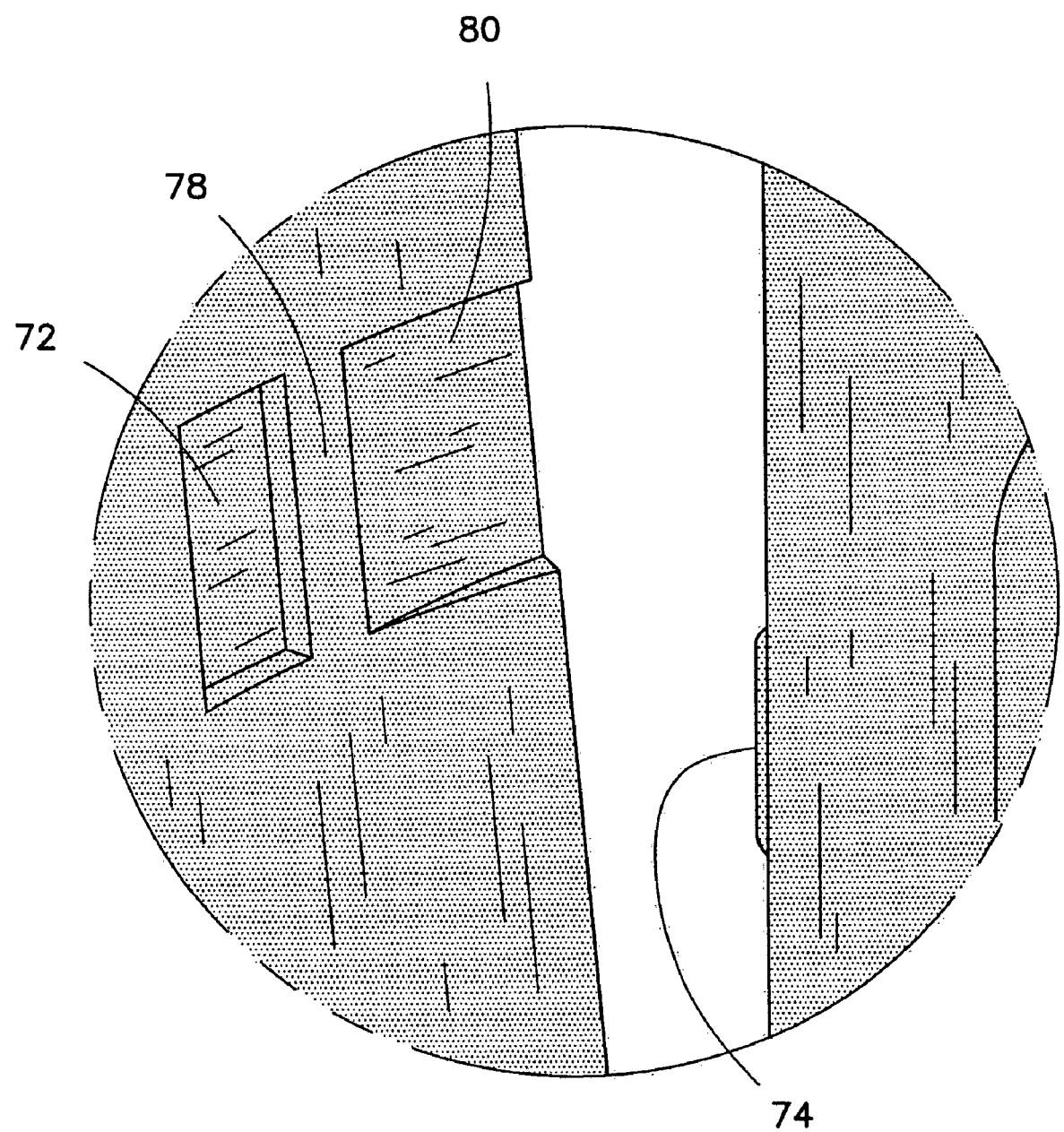
FIG. 8b is an enlarged fragmentary view of a locking mechanism in accordance with an embodiment of the present invention.

To prevent spring 62 from biasing trigger 24 and housing 22 beyond the home position and to prevent removal of trigger 24 by a user, trigger 24 includes a flange 58 that mates with an upstanding ridge 60. The inventive housing also includes a locking mechanism or "passive lock" that provides sufficient force to prevent the user from accidentally dispensing an article but not too much force to prevent intended dispensing. That is, the passive lock requires a greater force to overcome than that provided by spring 62. With reference to FIGS. 8a and 8b, trigger 24 defines a home cavity or recess 72 that receives an ear or protrusion 74 formed on back plate 76 (FIG. 4). When the user squeezes the dispenser, ear 74 must push past wall 78 (FIG. 8b) in order to move trigger 24 and housing 22 together. On the return stroke, ear 74 is guided by inclined recess 80 such that it smoothly traverses wall 78 and then snaps into place into cavity 12 from only the force of spring 62. It has been found that a depth of about 0.5 mm for cavity 72 provides a passive lock that provides sufficient force to prevent accidental dispensing.

Figure 6:
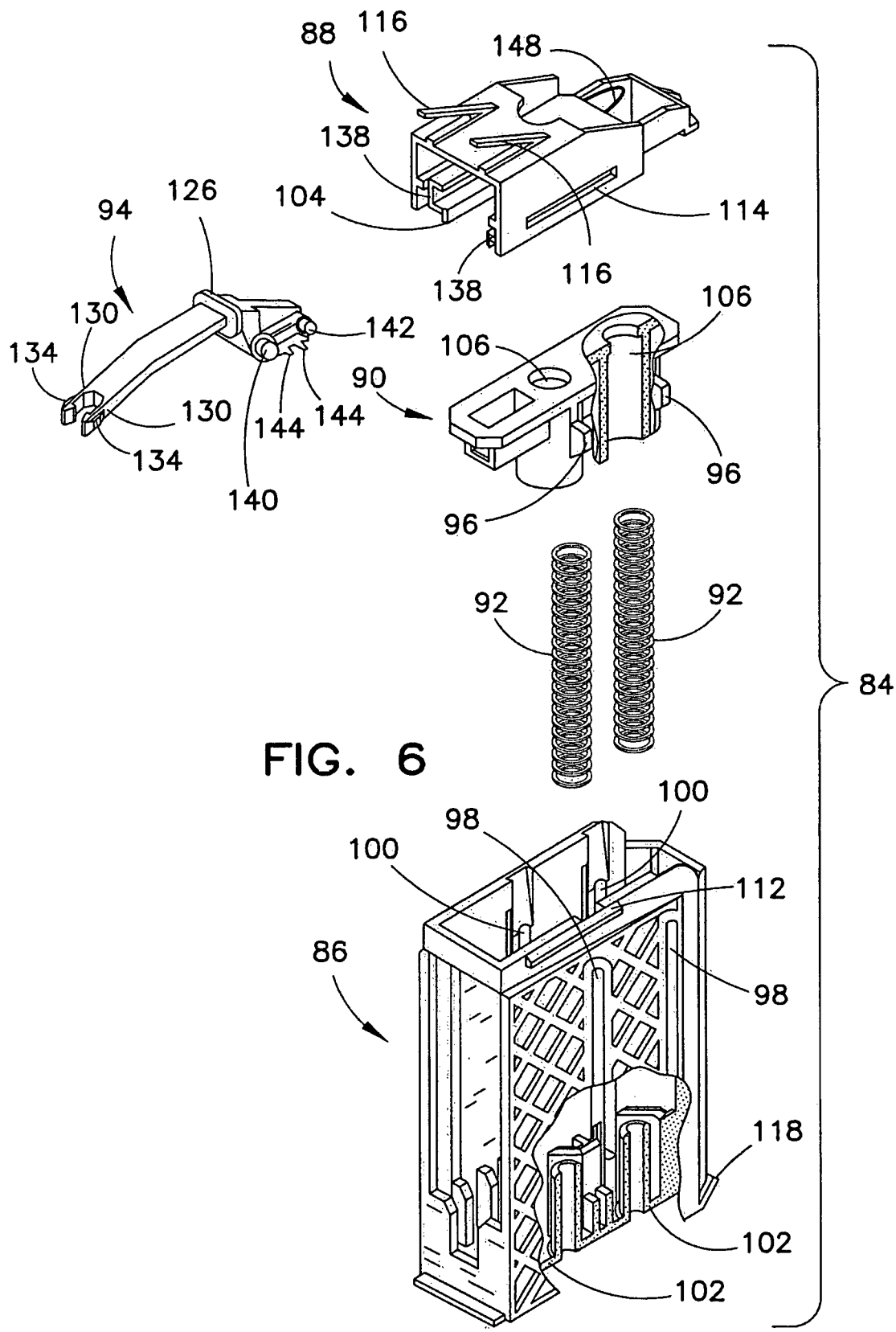
FIG. 6 is an exploded perspective view of a dispenser body or cassette in accordance with an embodiment of the present invention.

With reference to FIGS. 3, 4 and 6, a cassette 84 that carries stack 34 of test strips 30 is disposed within housing 22. The cassette is preferably made from a three-phase polymer that has moisture-absorbing properties, such as Active-Pak®, available from Capital Specialty Plastics, Auburn, Ala., 2AP®, available from Südchemie Performance Packaging Europe, Choisy le Roi, France, and Flotech® "S", available from Grace Davison, Worms, Germany. As noted above, the reagent materials contained in many test strips degrade when exposed to moisture, and housing them in a desiccant material such as cassette 84 helps address this issue.

The major components of cassette 84 include back plate 76, which is illustrated in FIG. 4, and hollow body 86, top cap 88, pressure pad 90, pressure pad springs 92 and flexible arm member 94, which are illustrated in FIG. 6. Pressure pad 90 carries the stack of test strips 34 and is movable vertically with respect to hollow body 86. Specifically, pressure pad 90 includes protrusions 96 that are slidingly received in guide slots 98. Two additional protrusions (not shown) extend from the back of pressure pad 90 and are slidingly received into guide slots 100 shown in FIG. 6. The protrusions and guide slots maintain the pressure pad aligned as it advances upward as test strips are dispensed. Once the protrusions reach the top end of the slots, further upward movement of pressure pad 90 is prevented, which would occur when the dispenser is empty. When test strips 30 are present in dispenser 20, upward movement of pressure pad 90 is limited by the uppermost strip abutting against shelves 104 formed in top cap 88. Similarly, the lowermost vertical position of pressure pad 90 occurs when the protrusions reach the bottom of the slots, which occurs when the cassette is filled to capacity with test strips. Cassette 84 preferably holds a range from five to one-hundred fifty of the test strips 34. In the illustrated embodiment, cassette 84 holds fifty test strips.

With further reference to FIG. 6, body 86 includes cylindrical spring retention posts 102 on which are received springs 92. Springs 92 extend into cylinders 106 formed in pressure pad 90, and their spring force biases the pressure pad upward as strips are dispensed. Top cap 88 is attached to hollow body 86 by means of anchor stanchions 112 that fit into slots 114. An opening 89 (FIG. 4) is formed between top cap 88 and hollow body 86 to allow a strip to exit the cassette. In the illustrated embodiment, the top cap is formed from polypropylene, although many other materials would be suitable. Spring fingers 116 provide pressure to seat the cassette subassembly in housing 22 as can be seen with reference to FIG. 7a. A toe clip 118 extending from the bottom of body 86 guides the cassette in place during assembly and fits under front rail 120 (FIG. 3) to hold the front of the cassette body 86 in the housing 22. Retention boss 122 retains the lower back half of the cassette subassembly in the housing 22.

Figure 5A:
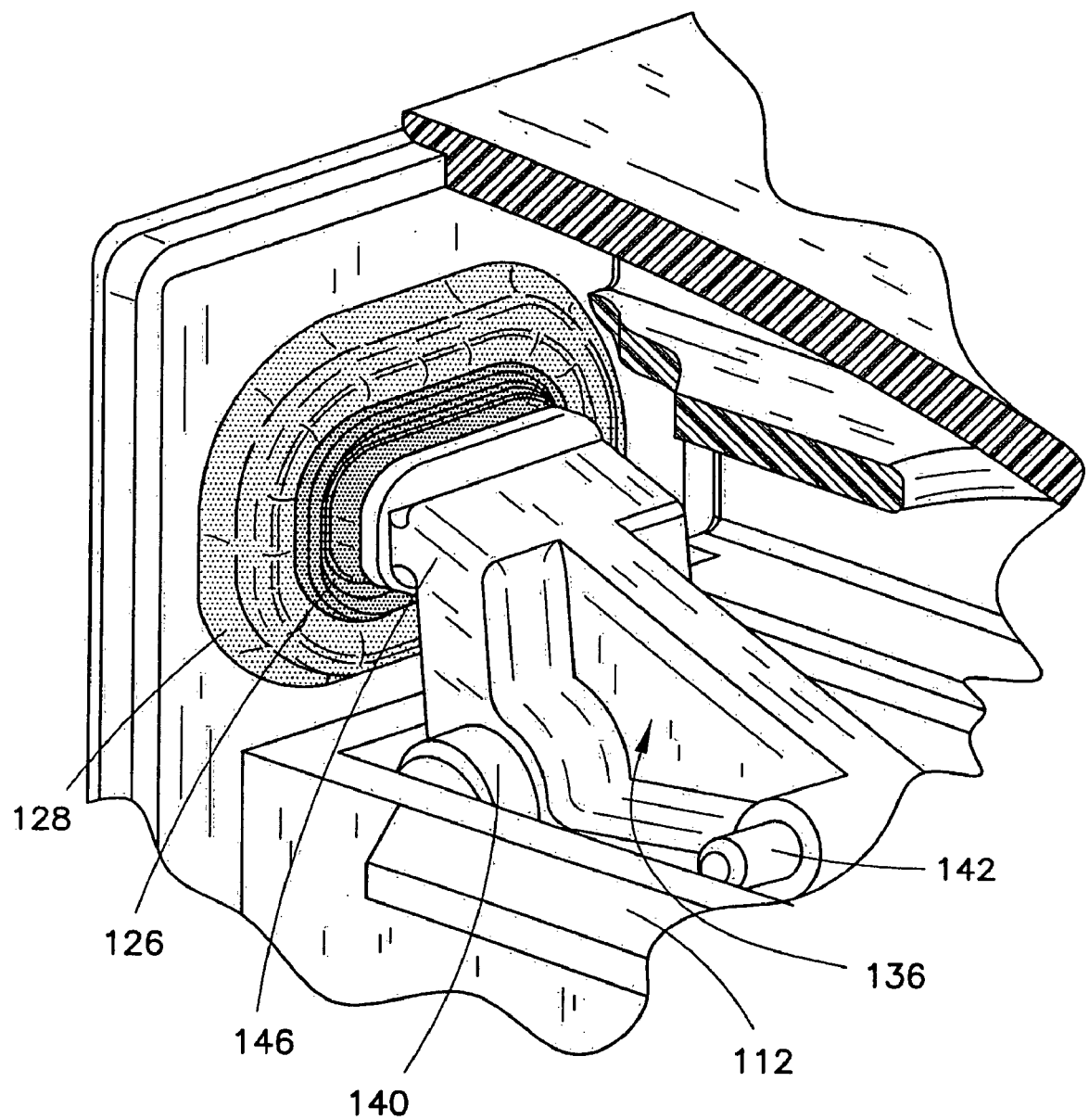
FIGS. 5a and 5b are an enlarged fragmentary perspective view and a sectional view, respectively, of a seal in accordance with an embodiment of the present invention.
Figure 5B:
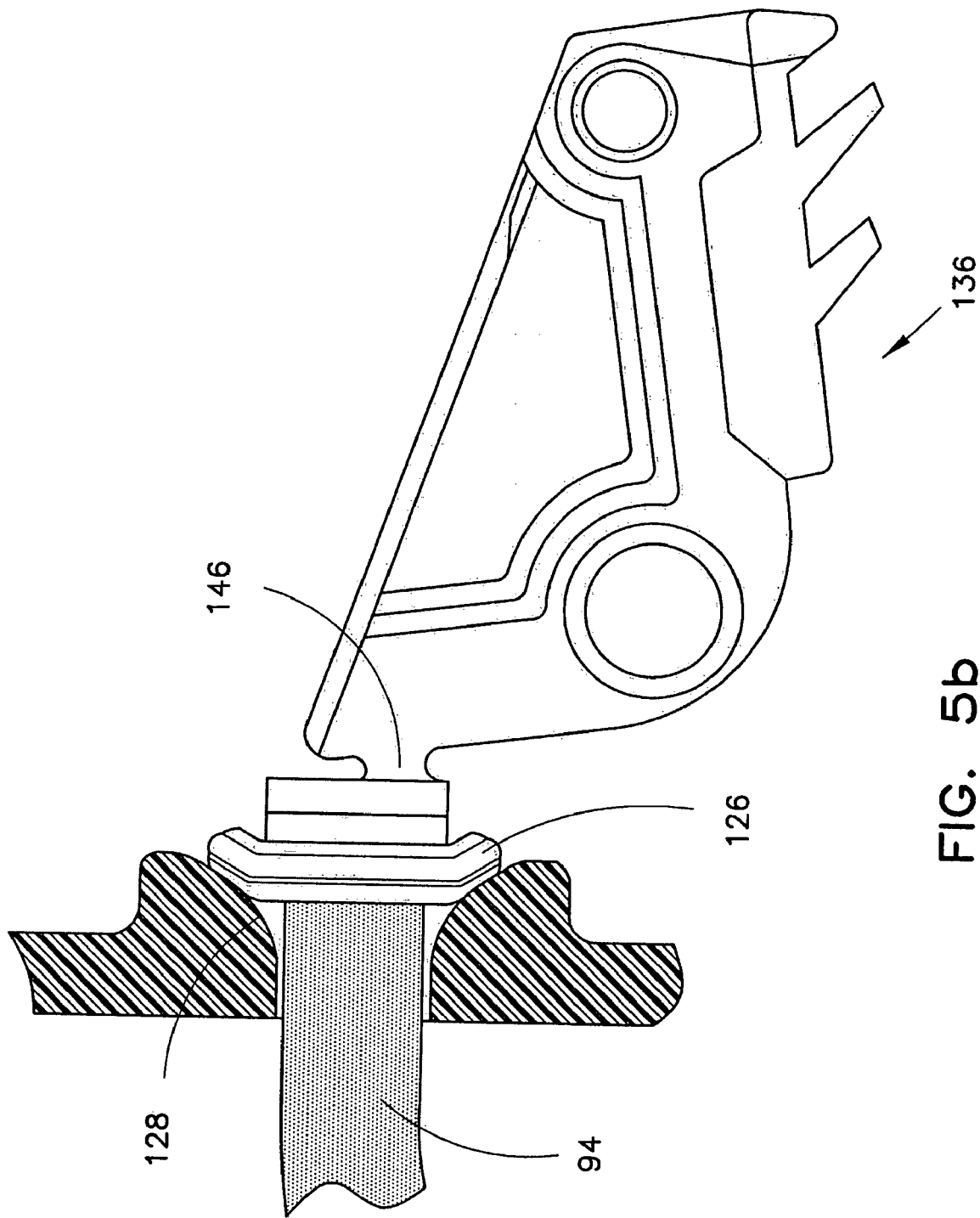

With further reference to FIG. 4, during assembly of dispenser 20, ribs 82 temporarily hold cassette 84 in place within housing 22. Back plate 76 is then welded to the main housing 22 and holds the cassette body 86 within housing 22, which means main housing 22 is essentially sealed from the ambient. The seal is only broken when aperture 124 in back plate 76 is unsealed while a test strip is being dispensed through lip seal 42. However, as shown in FIGS. 5a and 5b, flexible arm member 94 includes a sealing member 126 that engages a sealing surface 128 when dispenser 20 is in the home position. Sealing member 126 has an "umbrella" type geometry that circumscribes the flexible arm member and that flexes to conform to the conical recess shape of sealing member 128, thereby forming a tight seal. Sealing member 126 is preferably formed from Santoprene®. When the trigger 24 is squeezed, arm member 94 is actuated and the seal is temporarily broken until dispenser 20 returns to the home position.

In an alternate embodiment (not shown), sealing member 126 is attached to sealing surface 128, such that it stays in place when dispenser 20 is in the home and the dispensed positions. In this embodiment, the sealing member 126 is configured such that flexible arm member 94 passes through the sealing member 126 when the trigger 24 is squeezed. Sealing member 126 circumscribes the flexible arm member 94 but allows arm member 94 to slide through sealing member 126.

Figure 7A:
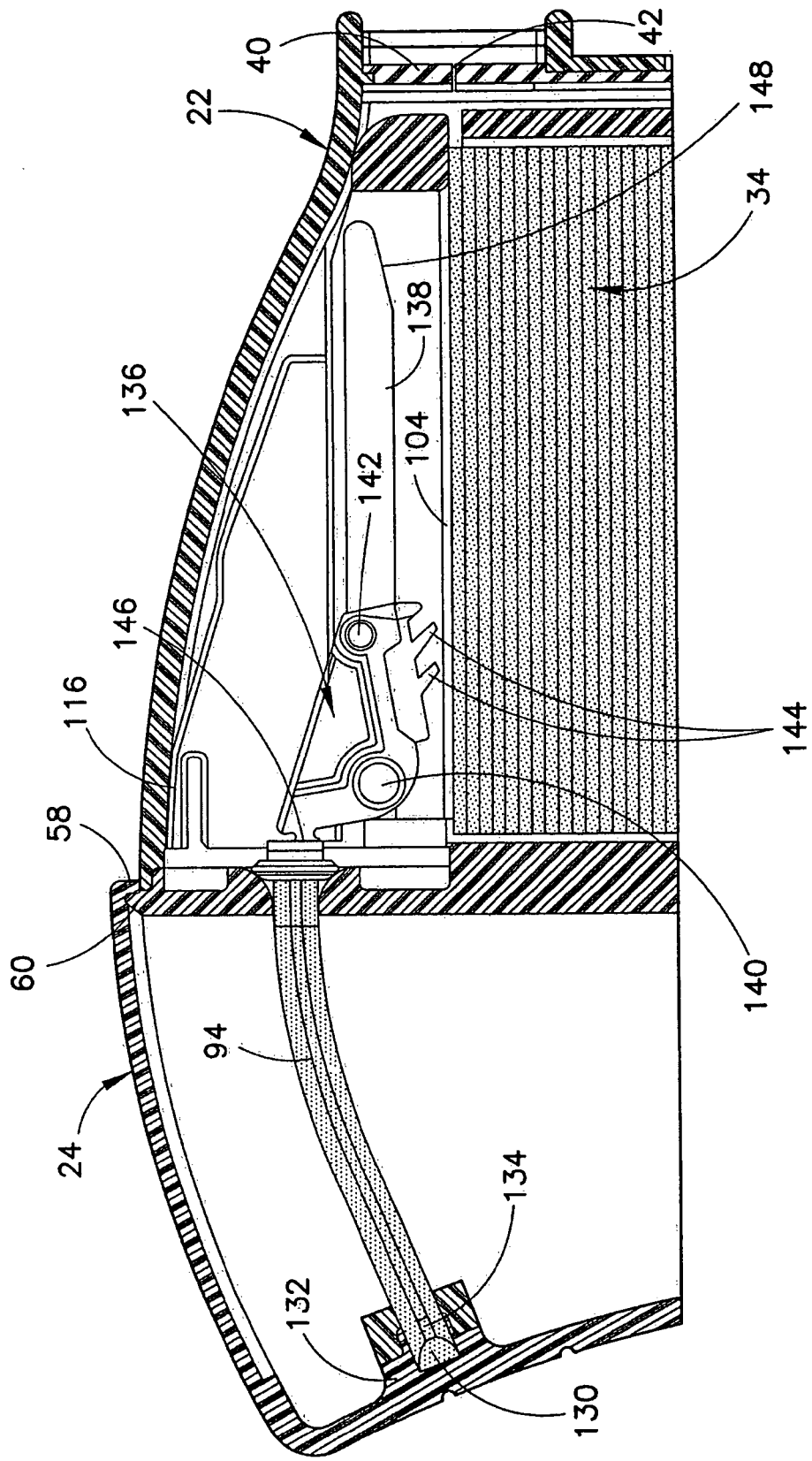
FIGS. 7a-7d are side sectional views that illustrate the movement of the dispenser of an embodiment of the present invention from the home position to the dispense position and then back.
Figure 7B:
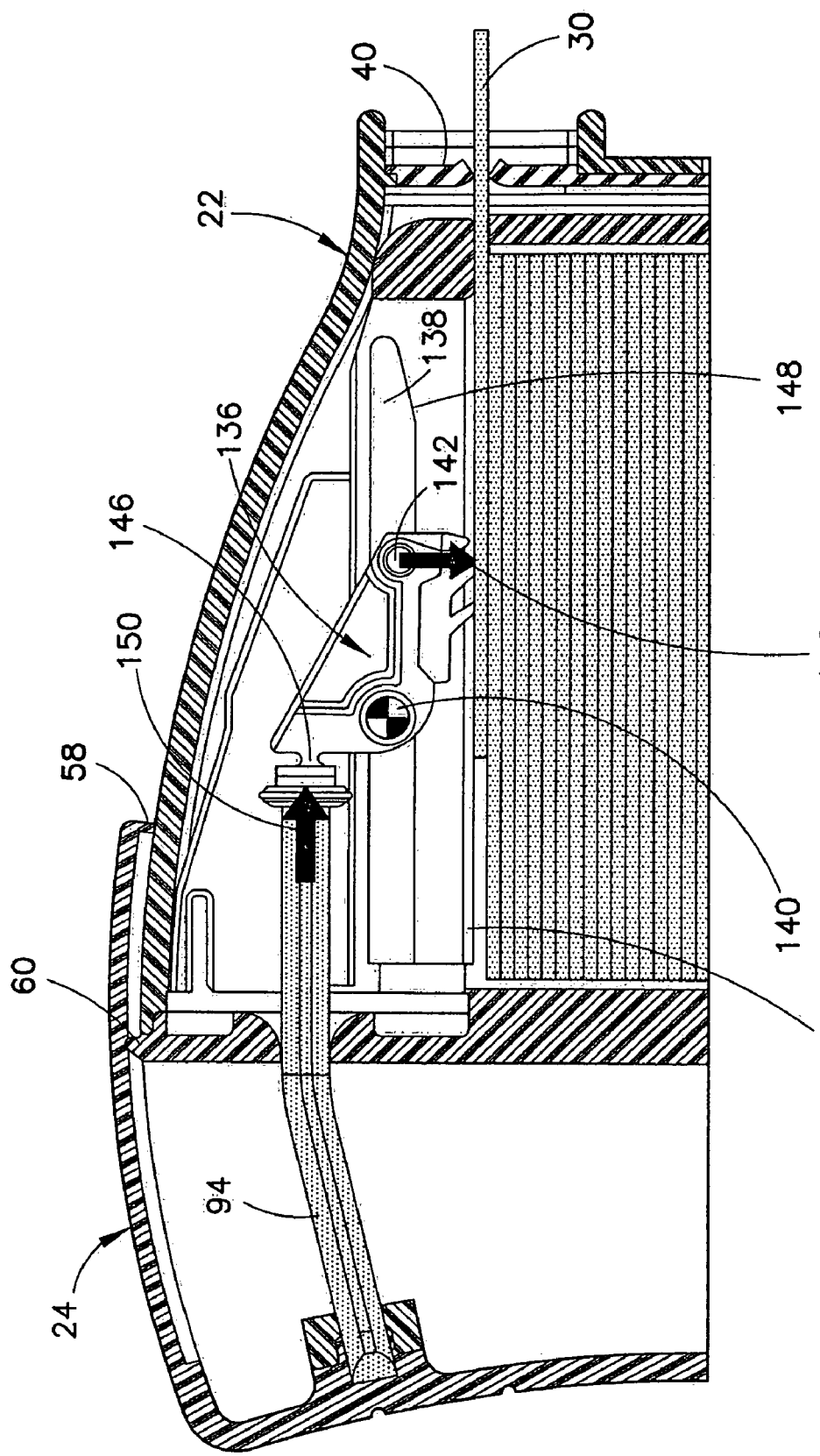
Figure 7C:
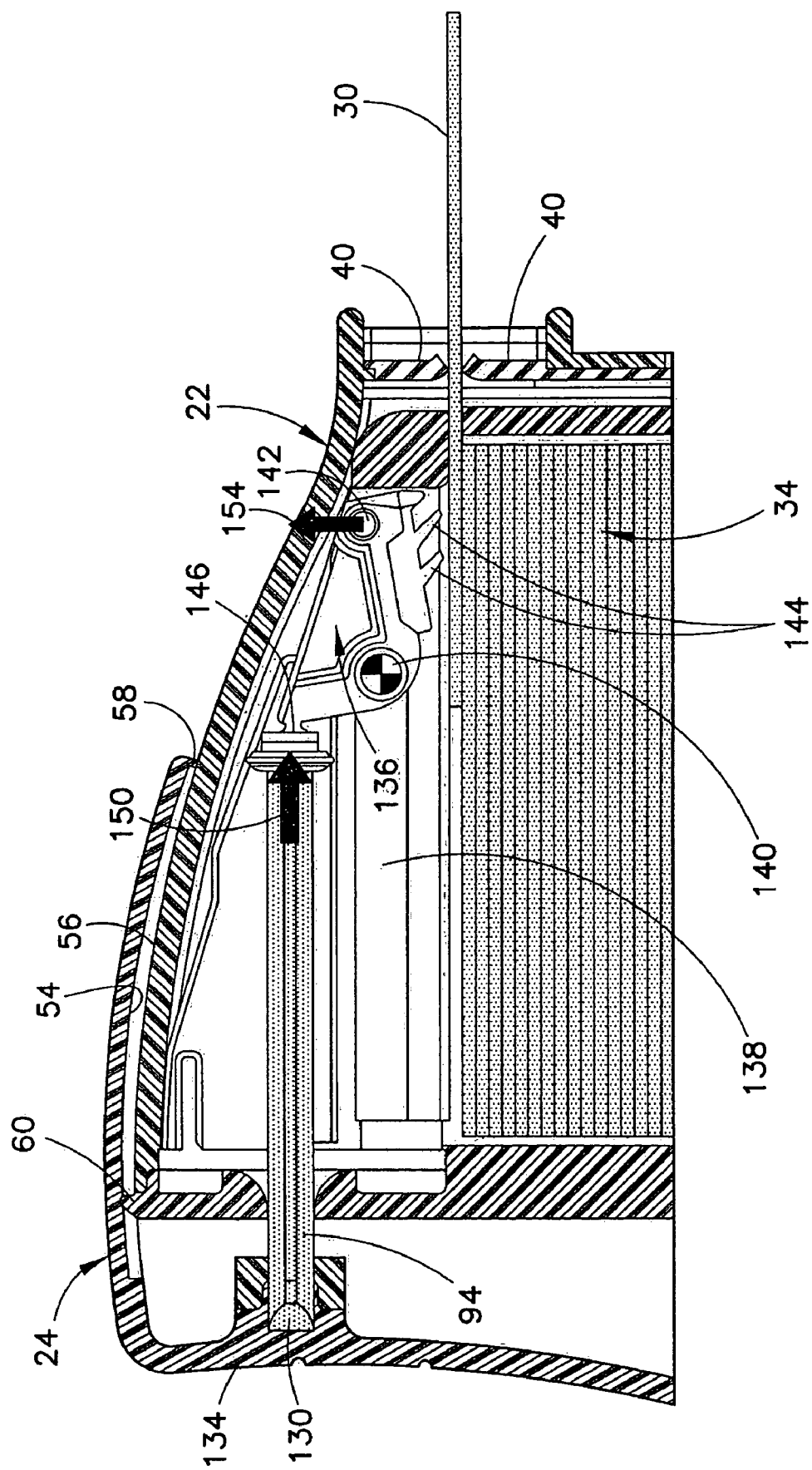
Figure 7D:
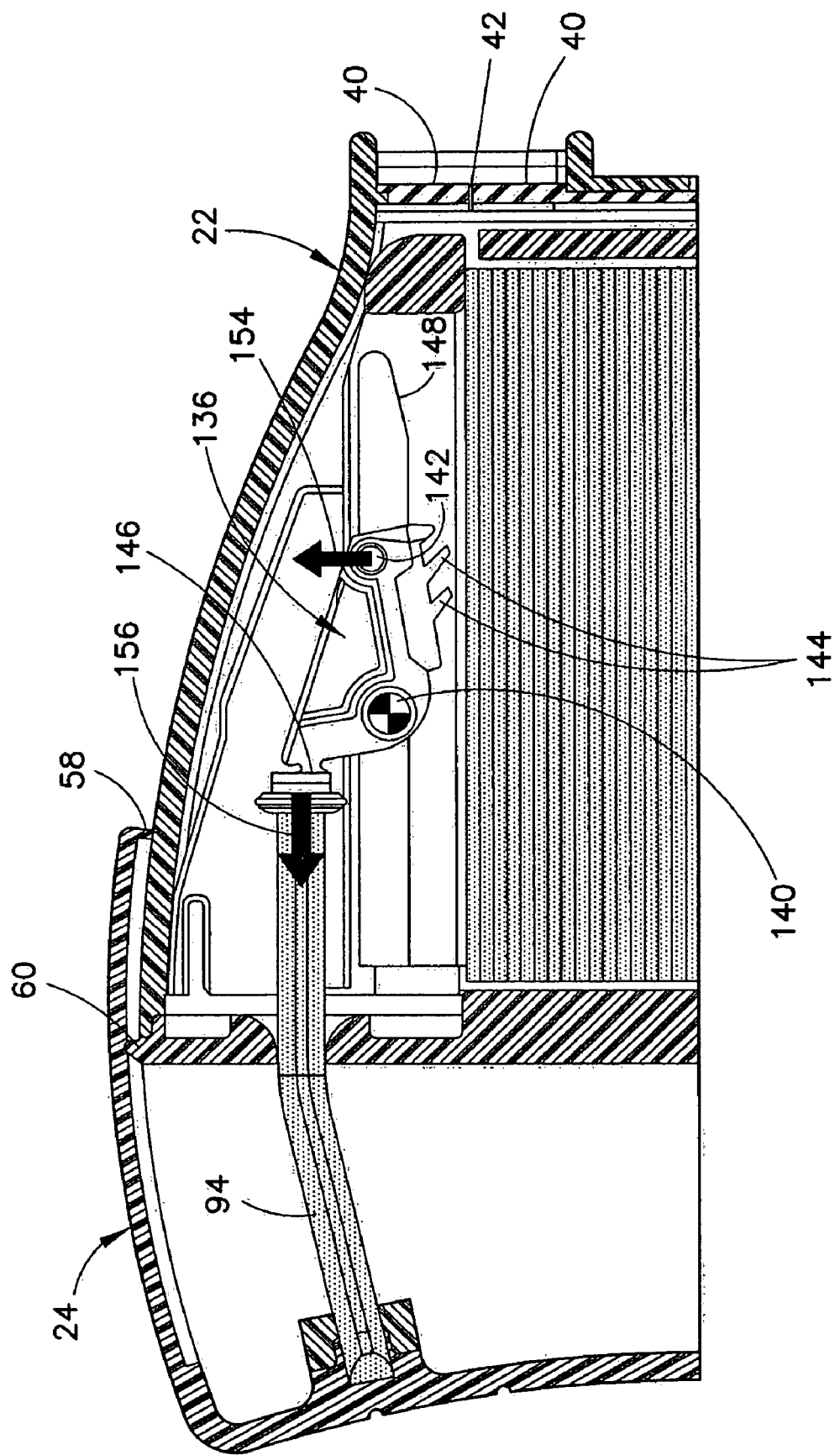
Figure 8C:
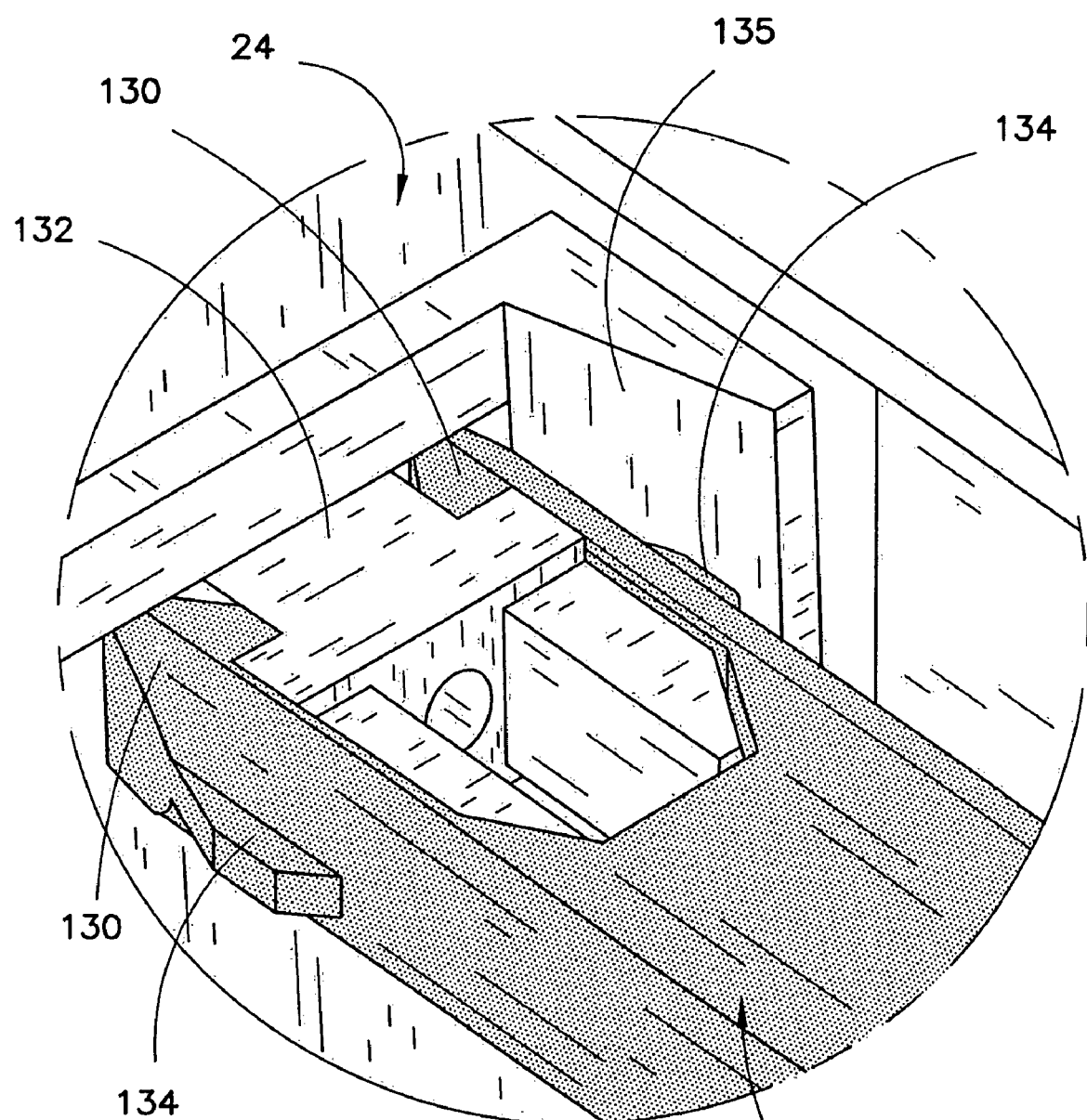
FIG. 8c is an enlarged fragmentary perspective view illustrating the connection of a flexible arm member to a trigger.

As shown in FIGS. 6-8, flexible arm member 94 is connected on one end to trigger housing 24 by means of clip fingers 130 that wrap around retention member 132. Ears 134 press against angled sides 135 of trigger housing 24 and prevent clips 130 from disengaging during operation of the dispenser. On its other end, the flexible arm member terminates in a pusher head 136 that is positioned above the test strips and is slidably disposed in groove 138. More particularly, pusher head 136 includes cams 140 and posts 142 extending into grooves 138. The cams, posts and grooves comprise part of a guiding mechanism that moves the pusher head up and down as it reciprocates, as described in more detail below. The pusher head also includes resilient fingers or engagement members 144 that frictionally engage the top surface of the top test strip and slide it out of the dispenser, as discussed in more detail below.

Pusher head 136 is preferably integrally formed with the remainder of flexible arm member 94 and is hingedly connected thereto by a "working hinge" 146. The working hinge provides stronger resistance than a normal "living hinge" but will still flex, allowing the pusher head to pivot or rotate down onto and up and away from the test strips. In the illustrated embodiment, the flexible arm member 94 is formed from polypropylene, but one of ordinary skill in the art could substitute many other flexible materials.

When not in use, the inventive dispenser is positioned in the "home" position depicted in FIGS. 1a and 7a. As the user begins to squeeze trigger 24 and housing 22 together, he or she must first overcome the "passive lock" described above. Thereafter, trigger 24 and housing 22 can be squeezed together against the force of spring 62, thereby defining a dispense stroke. Since flexible arm member 94 is coupled to trigger 24, the pivoting movement of the dispenser parts actuates the arm member and causes it to slide through aperture 124. The seal made by umbrella seal 126 is thus broken. Advantageously, however, arm member 94 has a profile that substantially matches that of aperture 124 such that arm member 94 engages the periphery of aperture 124 as it passes through it. A quasi-seal between arm member 94 and aperture 124 thus remains as arm member 94 slides through aperture 124. In other words, even though seal 126 moves away from aperture 124 when the dispenser is activated, because there is a close fit between arm member 94 and aperture 124, the seal there between is not significantly compromised.

Turning now to FIGS. 7a and 7b, this initial movement of the arm member causes pusher head 136 to pivot about cams 140 from a disengaged station spaced away from the stack of strips to an engaged station in which fingers 144 frictionally engage the top test strip. In other words, cams 140 define a pivot axis and the sliding movement in the direction of arrow 150 of arm member 94 as shown in FIG. 7b is translated through working hinge 146 and produces a moment about cams 140. This in turn causes pusher head 136 to pivot down as shown by arrow 152. At the same time, the pusher head slides to the right as shown and the top strip displaces flaps 40 of lip seal 42 as it exits the dispenser. Lip seal 42 maintains a quasi-seal even as strip 30 passes through it. Test strips 30 can be arranged in cassette 84 such that a dosing end or a meter insertion end of the test strip 30 exits first as the pusher head slides to the right.

As shown in FIG. 7b, groove 138 defines an inclined portion 148 at an end thereof. At the end of the dispense stroke, posts 142 are engaged by inclined portion 148, such that pusher head 136 pivots upward and away from the top test strip of the stack, as shown in FIG. 7c. This upward pivoting occurs despite there being a moment about cams 140 through the end of the dispense stroke. Advantageously, since pusher head 136 is pivoted away from the top test strip, the top strip can be easily pulled from dispenser 20 against only a slight frictional force produced by lip seal 42. The flexible arm member flexes into a substantially straight configuration at the end of the dispense stroke as shown in FIG. 7c. The bending or straightening of arm member 94 is due to the fact that the end of arm member 94 that is coupled to trigger 24 moves upward relative to housing 22 as the housing and trigger are squeezed together.

As the user loosens his or her grip and allows spring 62 to return trigger 24 and housing 22 to the home position, an opposite moment is created about cams 140 as shown in FIG. 7d. On the return stroke, the sliding movement in the direction of arrow 156 of arm member 94 as shown in FIG. 7d is translated through working hinge 146 and produces a moment about cams 140 which maintains the pusher head 136 in the disengaged position. Advantageously, even if the user loosens his or her grip before pulling the top strip completely from the dispenser, the pusher head will not engage this top strip on the return stroke. That is, the top strip will not retract on the return stroke simply because the user fails to pull it from the dispenser before releasing the trigger and housing.

It should be appreciated that after the strip is dispensed and the dispenser has returned to the home position, lip seal 42 has automatically returned to its sealed or closed position on its own volition, thereby making it unnecessary for the user to remember to close the dispenser.

Optionally, the dispenser 20 can be integrated with a test meter that reads the test strips. The meter can also receive data from the test strip 30 and/or dispenser 20 and interpret the data. Dispenser 20 can be configured with a radio frequency identification (RFID) tag that stores information about the strips such as lot number, expiration date, type of test strip, among other information. The meter can be configured with an RFID reader which sends a signal to the RFID tag when the dispenser is brought within close proximity of the meter. The meter can thus receive the data that is stored on the RFID tag.

RFID technology is known in the art and need not be described in further detail herein.

Figure 9A:
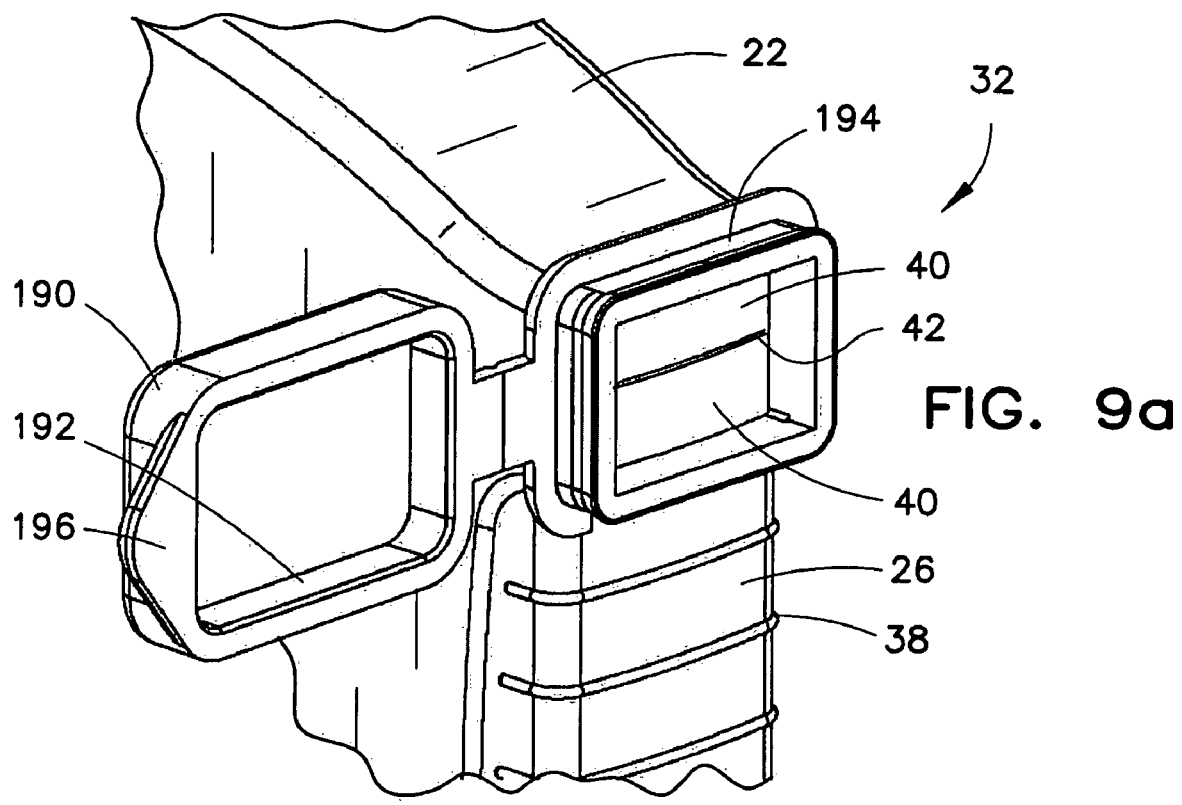
FIGS. 9a and 9b are enlarged fragmentary perspective views illustrating a lip seal cover in accordance with an embodiment of the present invention.
Figure 9B:
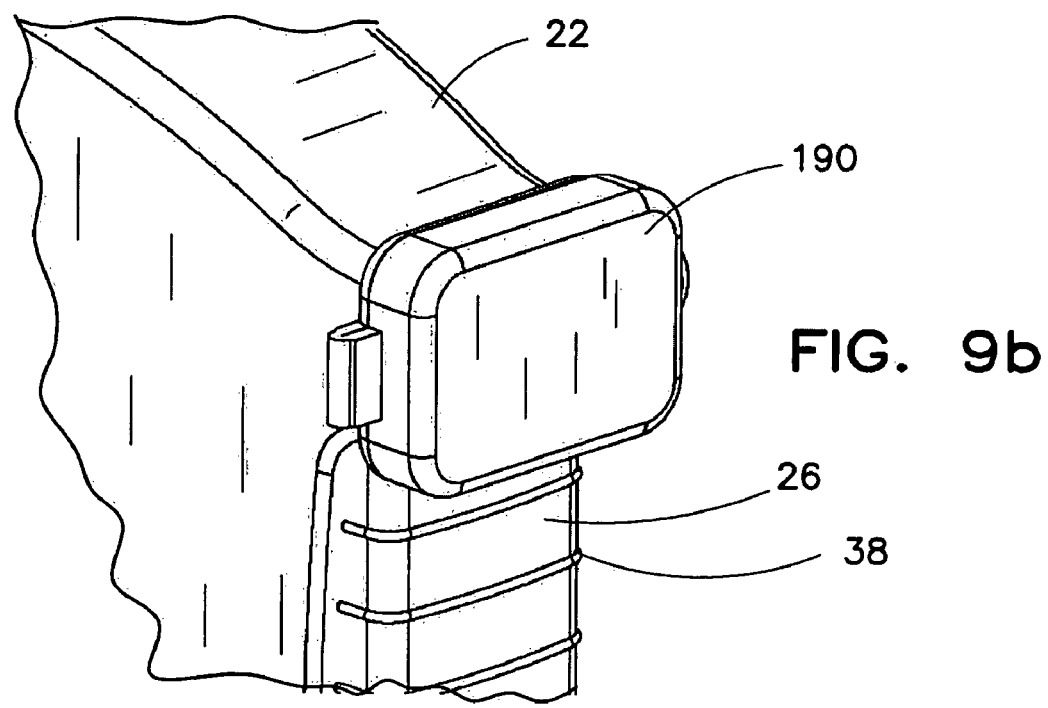

In the illustrated embodiment in FIGS. 9a-9b, housing 22 includes a lip seal cover 190 for covering the exit 32. Lip seal cover 190 has an inner surface 192 that defines a receptacle that receives protruding lip 194 of exit 32 by a friction fit engagement. As shown, the lip seal cover 190 is hingedly connected to housing 22. However, other means for making the connection between lip seal cover 190 and exit 32, e.g., a snap-on connection, could be substituted for the hinge connection. When the dispenser is in use, the lip seal cover 190 is pivoted away from the exit 32 by the user applying a finger or thumb to tab 196, which exposes the flaps 40 of lip seal 42, as shown in FIG. 9a. When the dispenser is not in use, the lip seal cover 190 is positioned over the exit 32 to cover the flaps 40 of lip seal 42 as shown in FIG. 9b. Lip seal cover 190 may be formed of any number of materials such as plastics, composites, metals and the like. Advantageously, lip seal cover 190 acts as a dust cover for exit 32 and protects exit 32 from contact damage by items such as keys, coins, cosmetic containers, and the like when the dispenser is carried in a pocket or container having such items.

Figure 10A:
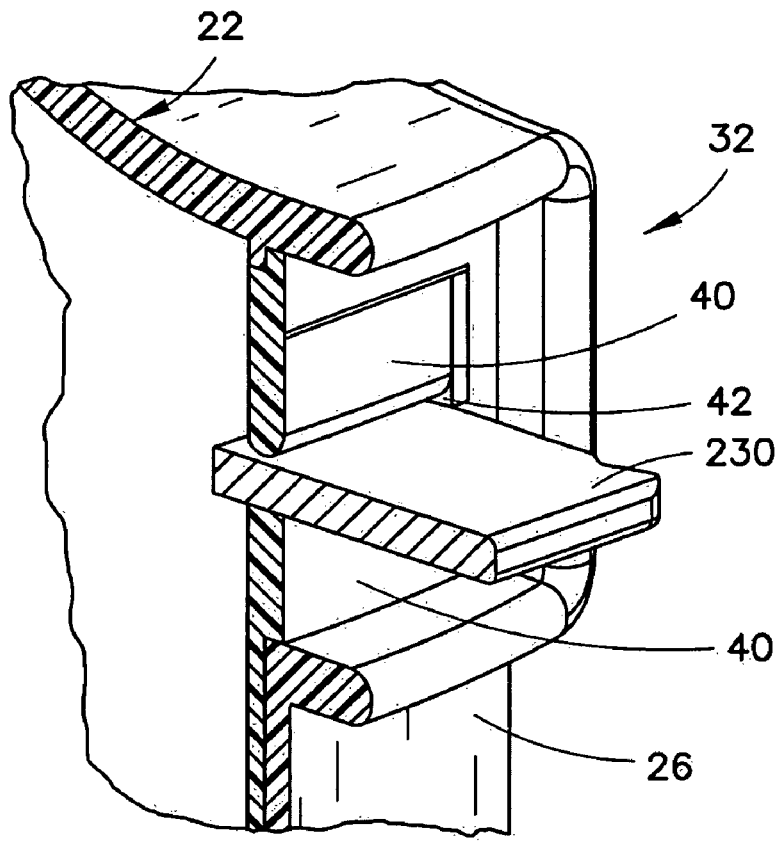
FIGS. 10a and 10b are enlarged fragmentary perspective views in partial cross section illustrating a platform and a lip seal in accordance with an embodiment of the present invention.
Figure 10B:
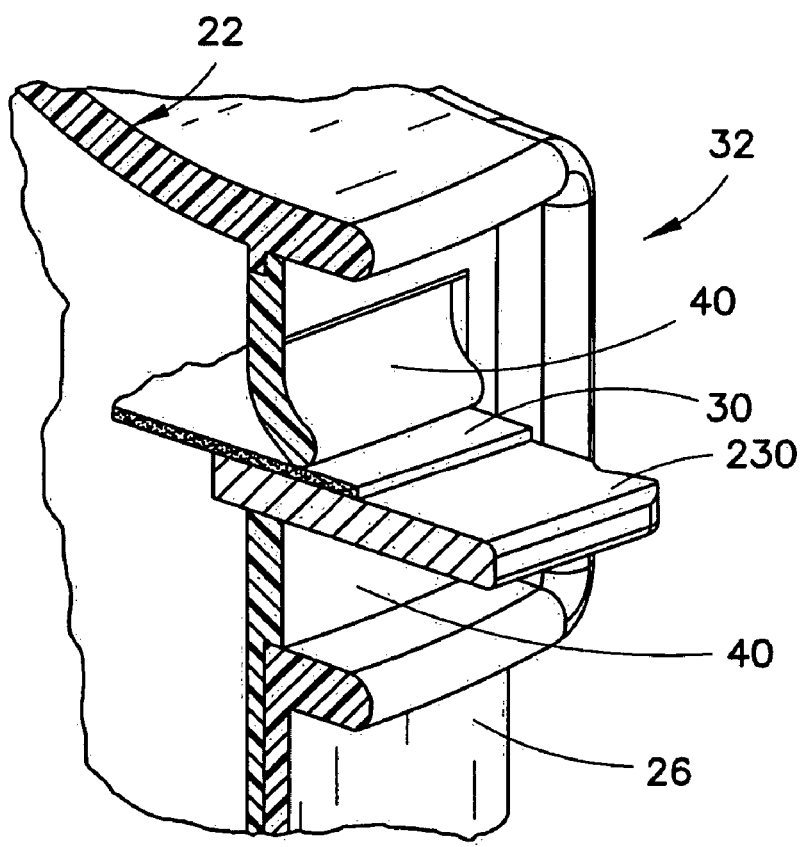

In the embodiment illustrated in FIGS. 10a-10b, housing 22 includes a platform 230 inserted between flaps 40 of lip seal 42 and integrally attached to the housing 22. The platform 230 is sized to fit within the lip seal 42 as shown in FIG. 10a. When the dispenser is not in use, the platform 230 inserted between the flaps 40 acts as a plug and forms an airtight seal with the flaps 40. As shown in FIG. 10b, when dispensing the first test strip 30 from the dispenser, the test strip 30 displaces or biases the top flap outwardly as it exits the dispenser. Thereafter, top flap 40 will remain in an outward position, but remains nonetheless biased against platform 230. The platform 230 provides a surface that the test strip 30 can ride on or slide over as the test strip 30 passes through the lip seal 42. It should be appreciated that the dispenser could be configured to dispense test strips between the bottom flap and the platform or the top flap and the platform. Platform 230 may be formed of any number of materials such as plastics, composites, metals or other materials.

Figure 11A:
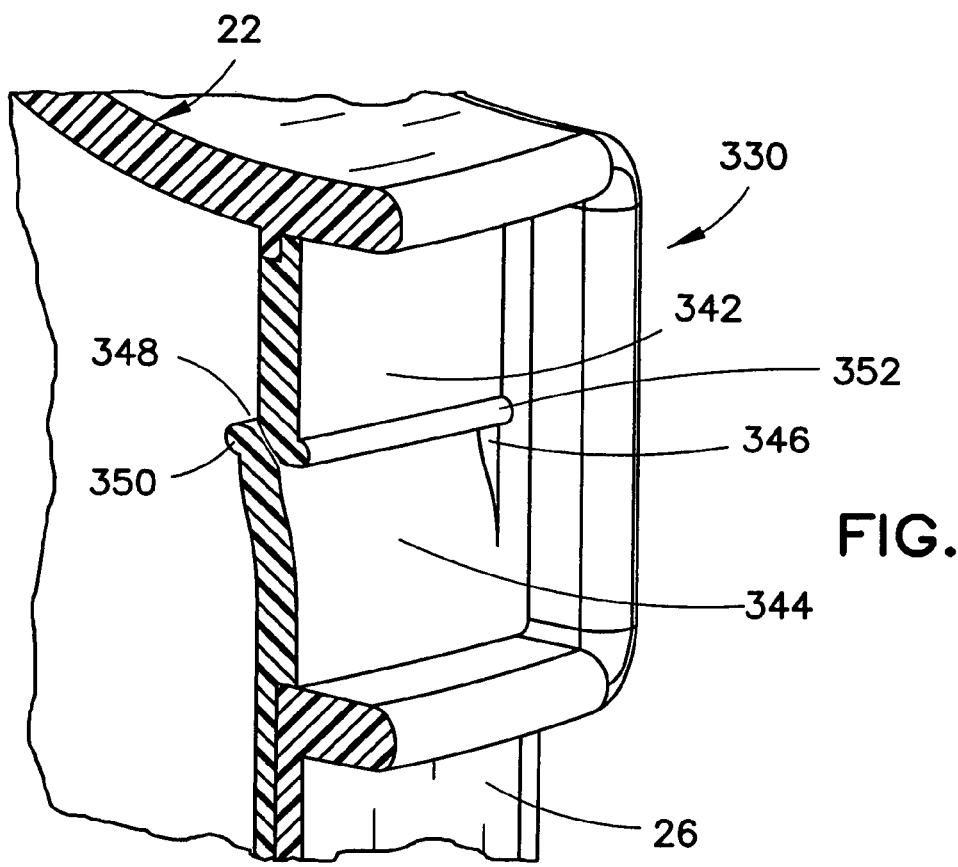
FIGS. 11a and 11b are enlarged fragmentary perspective views in partial cross section illustrating a lip seal and a reconfigured lip seal, respectively, in accordance with an embodiment of the present invention.
Figure 11B:
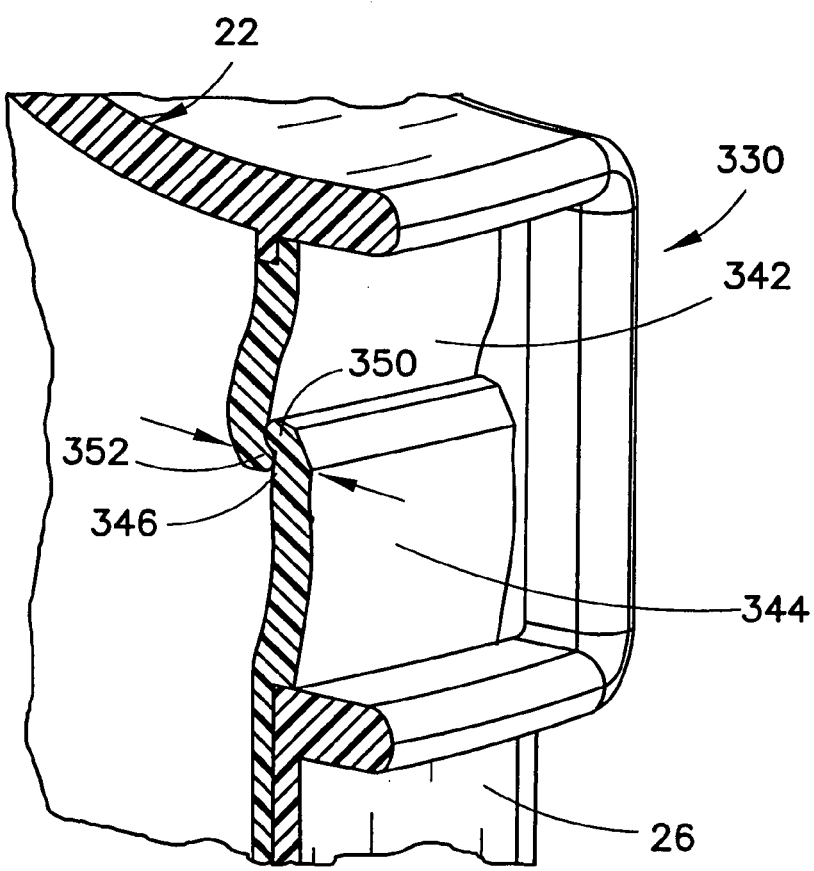

As shown in FIGS. 11a-11b, housing 22 includes an exit 330 that can be reconfigured to form an airtight seal. To achieve manufacturing efficiency, it is desirable to form seal 346 in a single step, e.g., by injection molding. It is further desirable to form ribs 38 (FIG. 2) integrally with seal 346. One of the drawbacks of injection molding is that discontinuities such as lip seal 42 require a part in the mold that separates flaps 342 and 344 that are to be formed with the mold. If the seal 346 is to be integrally formed, it will thus include a small gap such as gap 348 illustrated in FIG. 11a between the two flaps.

As formed, seal 346 depicted in FIG. 11a is unsuitable because it is not air-tight. Recognizing that a gap will be present in the originally molded part, the seal 346 shown in FIG. 11a is designed so that it can be "inverted" or "reconfigured" after initially being molded to form an airtight seal in which the two flaps not only contact one another, but are biased together. Specifically, bottom flap 344 is angled to the left or inwardly of the dispenser and includes a nub 350 that points to the left or inside of the dispenser. Flap 342 is preferably angled opposite to flap 344 and also includes a nub 352 that points outwardly or to the right as shown in FIG. 11a. However, after molding, the flexible seal 346 can be reconfigured by inverting the position of the flaps such that flap 342 and flap 344 are biased against each other to form an airtight seal as shown in FIG. 11b. For example, in FIG. 11a, a force can be applied to the top flap 342 to push the top flap 342 to the left and over the bottom flap 344 and/or a force can be applied to the bottom flap 344 to push the bottom flap 344 to the right and under the top flap 342. Alternatively, the airtight seal shown in FIG. 11b can be formed by ejecting the first test strip from dispenser 20, during which the test strip will push flap 344 to the right, past flap 342. When the test strip is fully removed from the dispenser, the configuration shown in FIG. 11b will be achieved.

Since flap 342 as molded tends to point to the right and flap 346 as molded tends to point to the left, inverting the seal to the configuration shown in FIG. 11b creates an advantageously airtight seal in which the flaps are pressed against one another. As shown reconfigured in FIG. 11b, the top flap 342 is displaced to the left of bottom flap 344. Further, the top flap 342 and the bottom flap 344 are biased together as shown by the arrows in FIG. 11b. When dispensing a test strip, the test strip displaces or biases apart the bottom flap 344 from the top flap 342 as it passes between the flaps and exits the dispenser. As described with reference to other embodiments, seal 346 can be formed from Santoprene® or another elastic material that allows top flap 342 and bottom flap 344 to flex or bend. Additionally, the flexible seal 346 can be covered with a cap (see FIG. 9a).

Figure 12A:
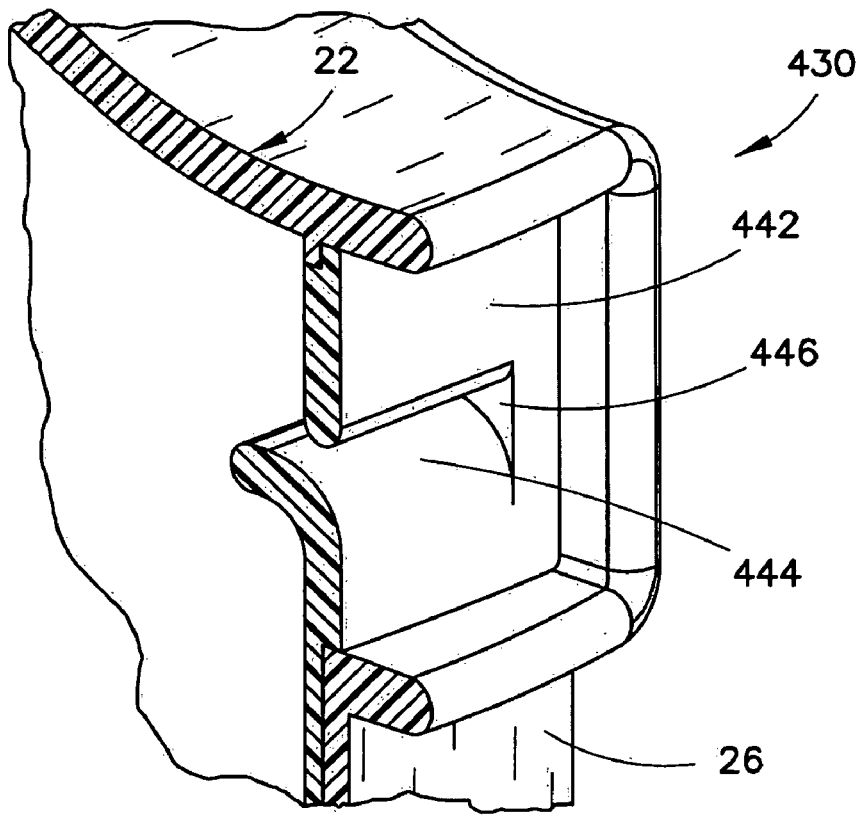
FIGS. 12a and 12b are enlarged fragmentary perspective views in partial cross section illustrating a lip seal and a reconfigured lip seal, respectively, in accordance with an embodiment of the present invention.
Figure 12B:
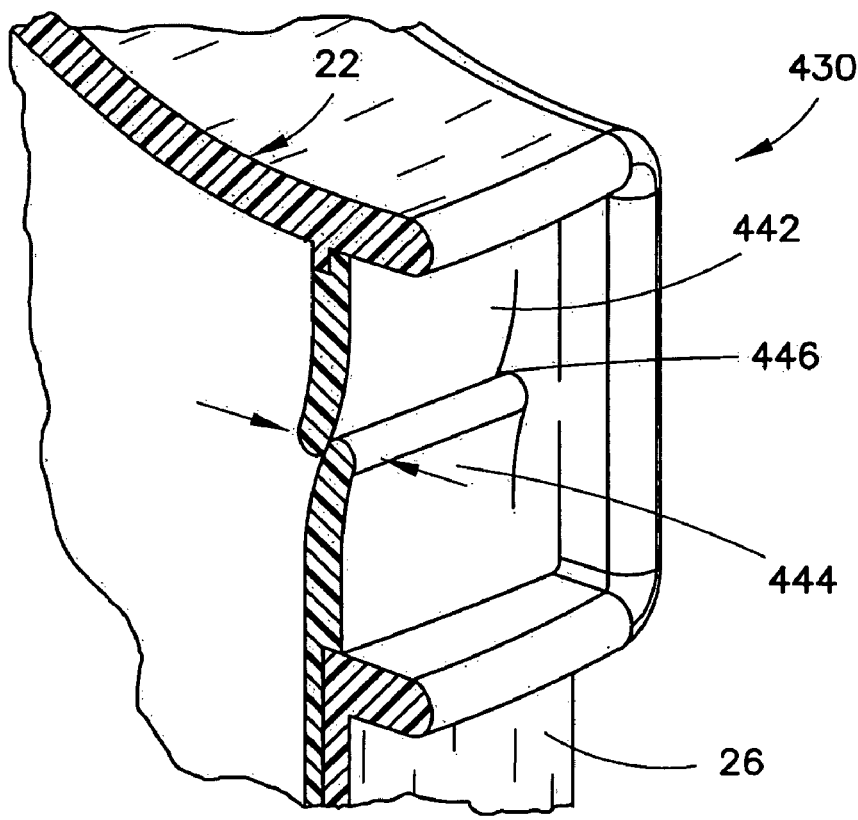

In the embodiment illustrated in FIGS. 12a-12b, housing 22 includes an exit 430 that can be reconfigured to form an airtight seal. As shown in FIG. 12a, exit 430 as molded includes top flap 442 and bottom flap 444 that form a flexible seal 446. The bottom flap 444 is positioned initially to the left of top flap 442. In this configuration, top flap 442 and bottom flap 444 are substantially in the same position as when the flexible seal 446 was formed or molded. The flexible seal 446 can be reconfigured by inverting the positions of the flaps such that flap 442 and flap 444 are biased against each other. For example, a force can be applied to the bottom flap 444 shown in FIG. 12a to push or pull it to the right and under the top flap 442.

As shown reconfigured in FIG. 12b, the top flap 442 is displaced to the left of bottom flap 444. Further, the top flap 442 and the bottom flap 444 are biased together as shown by the arrows in FIG. 12b. When dispensing a test strip, the test strip displaces or biases apart the bottom flap 444 from the top flap 442 as it passes between the flaps to exit the dispenser. Top flap 442 and bottom flap 444 can be formed from Santoprene® or another elastic material that allows top flap 442 and bottom flap 444 to flex or bend. Further, top flap 442 and/or bottom flap 444 can be integrally formed with ribs 38 (see FIGS. 1 and 2). Additionally, the flexible seal 446 can be covered with a cap (see FIG. 9a).

Figure 13:
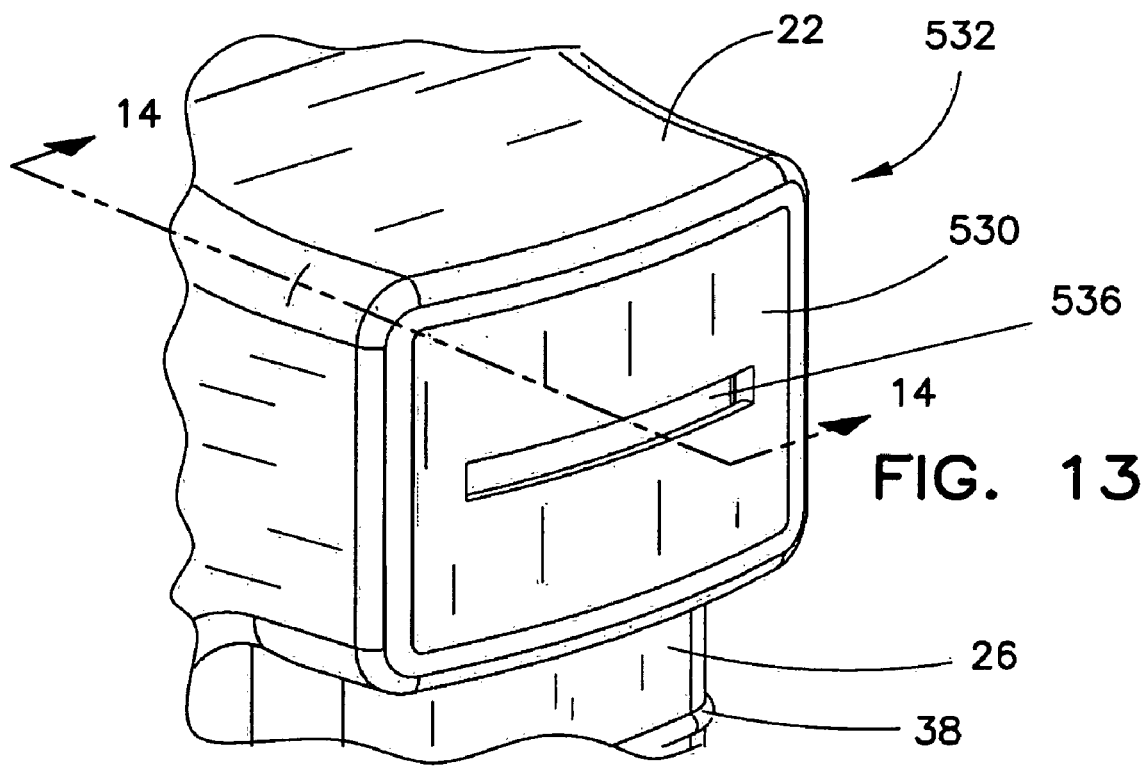
FIG. 13 is an enlarged fragmentary perspective view illustrating a cap in accordance with an embodiment of the present invention.
Figure 14:
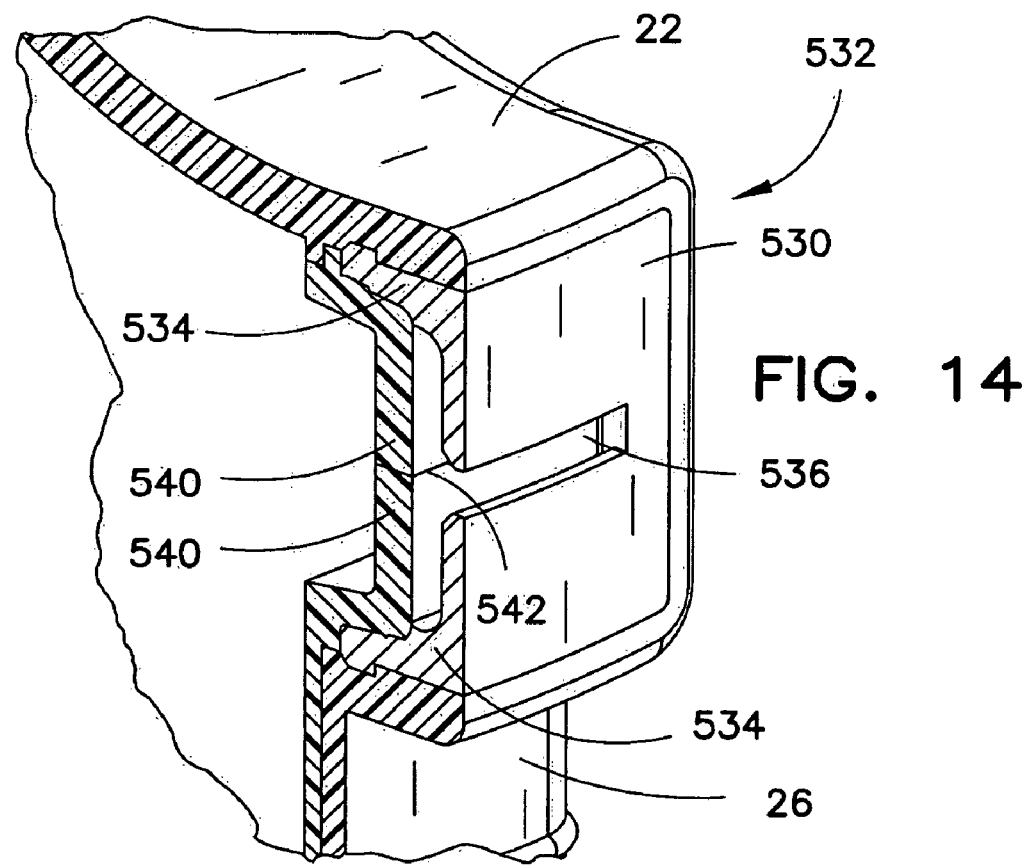
FIG. 14 is an enlarged fragmentary perspective view in partial cross section illustrating a cap and an exit in accordance with an embodiment of the present invention.

In the embodiment illustrated in FIGS. 13-14, housing 22 includes a cap 530 for covering exit 532. Cap 530 has an outer periphery that substantially matches that of exit 532 but is slightly smaller, such that cap 530 fits snugly within the periphery defined by exit 532. Cap 530 includes an opening 536 from which test strips 30 are dispensed. Cap 530 may be formed of any number of materials such as plastics, composites, metals or other materials. Cap 530, like lip seal cover 190, also acts as a dust cover for exit 532 and protects exit 532 from contact damage by foreign objects.

Exit 532 includes flaps 540 that form a flexible seal 542 as shown in FIG. 14. Further, biasing members 534 are wedged between the housing 22 and the flaps 540 to reconfigure the flexible seal 542 as shown in FIG. 14 such that the biasing members 534 bias the flaps 540 together to form an airtight seal. That is, as cap 530 is installed into dispenser 20, wedge-shaped biasing members 534 are inserted between the housing 22 and seal 542 such that biasing members 534 squeeze the flaps 540 together. As shown, biasing members 534 are integrally formed with cap 530. When dispensing a test strip, the test strip displaces or biases apart the flaps 540 as it passes between the flaps 540 to exit the dispenser through opening 536. Flaps 540 can be formed of Santoprene® or another elastic material that allows the flaps 540 to flex or bend. Also, it should be appreciated that the embodiment shown in FIGS. 9a-9b can also be configured to include biasing members that squeeze the flaps together.

Figure 15A:
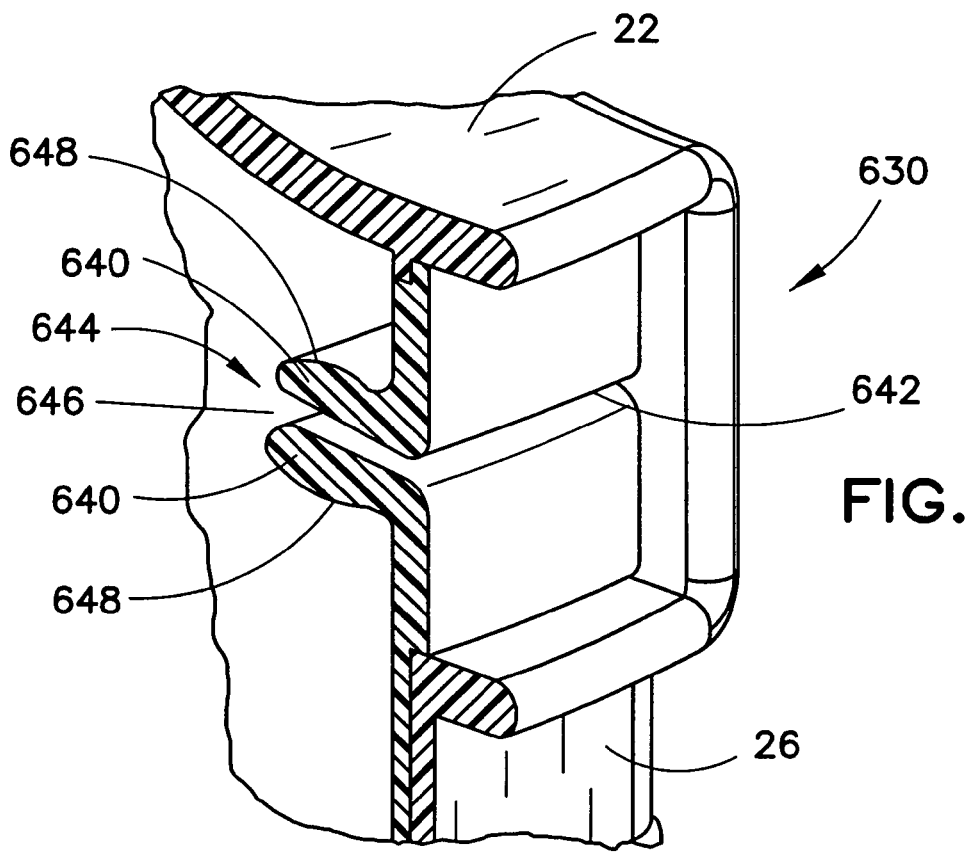
FIGS. 15a-15c are enlarged fragmentary perspective views in partial cross section illustrating a flexible seal, a reconfigured flexible seal, and a reconfigured flexible seal with an article exiting the seal, respectively, in accordance with an embodiment of the present invention.
Figure 15B:
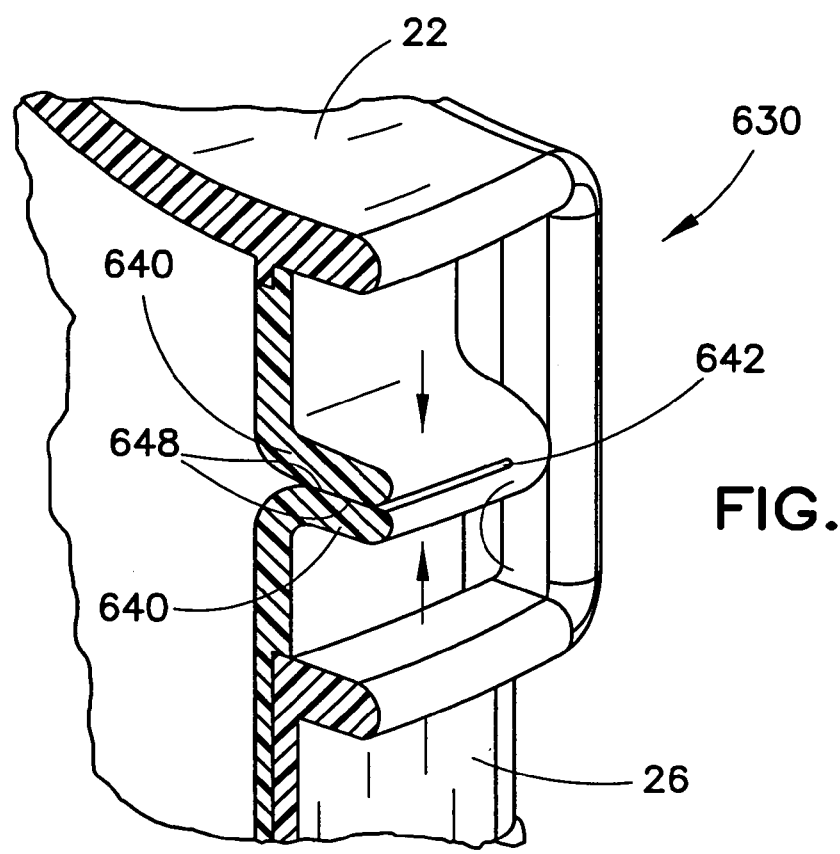
Figure 15C:
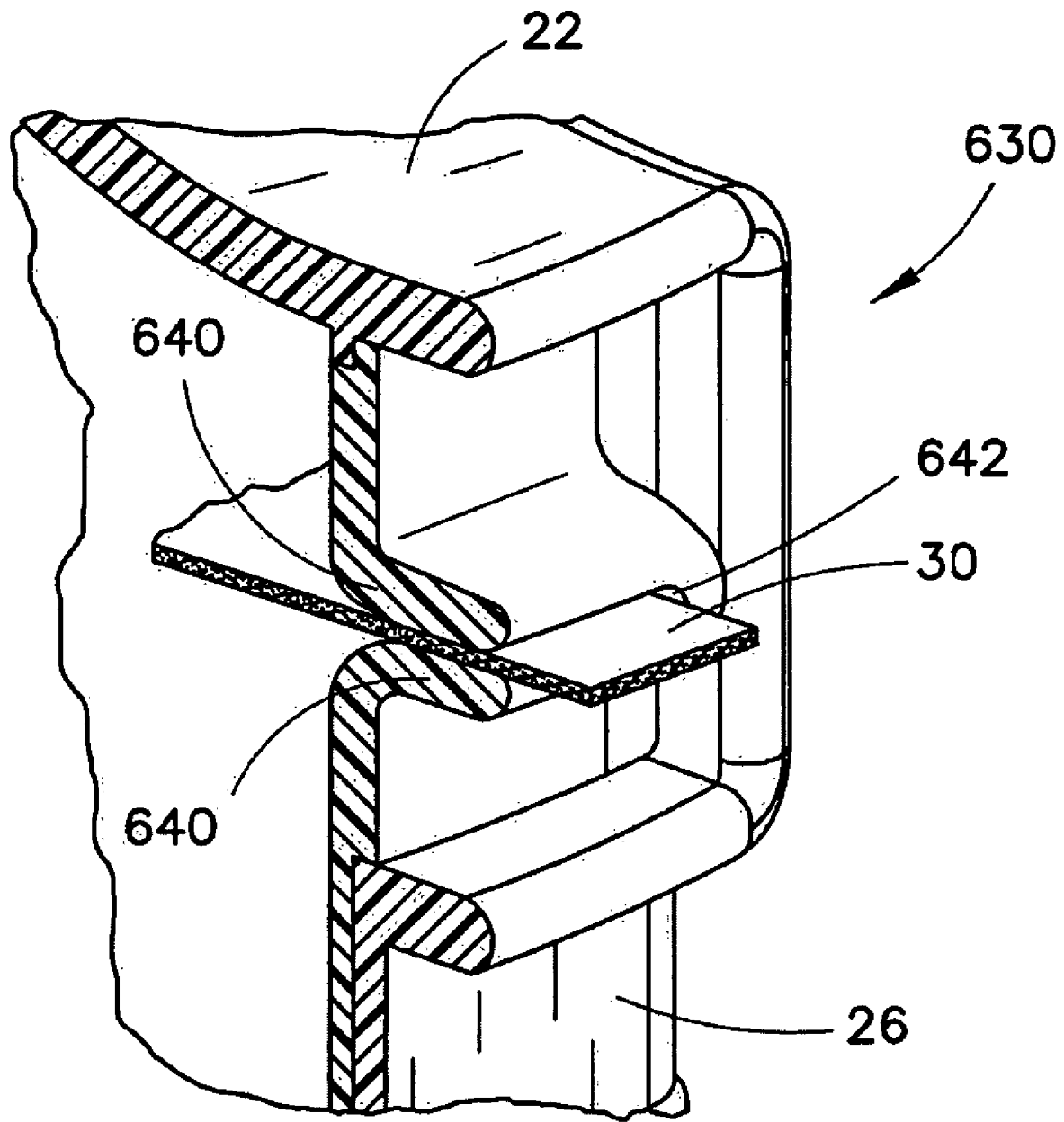

As shown in FIGS. 15a-15c, housing 22 includes an exit 630 that can be reconfigured to form a substantially or completely airtight "duckbill" seal. Exit 630 is shaped as a duckbill with walls 640 that form an elongated channel 644, as illustrated in FIG. 15a. The walls 640 point to the left in FIG. 15a. In this configuration, walls 640 are substantially in the same position as when the flexible seal 642 was formed or molded. As described elsewhere, since the seal 642 is preferably integrally formed by injection molding, the walls 640 define a gap 646 therebetween when the part leaves the mold from which it is made. However, the gap 646 can be eliminated by inverting or turning the duckbill seal 642 inside out, as can be appreciated by comparing FIGS. 15a and 15b. The curved or profiled outer sides 648 of walls 640 shown in FIG. 15a become the inner walls of the seal shown in FIG. 15b, in which the walls 640 are biased together and form an air-tight seal, as indicated by the arrows in FIG. 15b. The profiled shape of walls 640 shown in FIG. 15a enhances the bias between walls 640 when the seal 642 is turned inside out to form the structure shown in FIG. 15b.

When dispensing test strip 30 as shown in FIG. 15c, the test strip 30 displaces or pushes apart the top wall from the bottom wall as it passes between the walls 640 to exit the dispenser. Walls 640 can be formed from Santoprene® or another elastic material that allows the walls 640 to flex or bend. Further, walls 640 can be integrally formed with ribs 38 (see FIGS. 1 and 2). In addition, the flexible seal 642 can be covered with a cap (see FIG. 9a).

In certain embodiments, the dispenser can be configured to facilitate inserting a strip into a meter without the need for the user to have to touch a strip. For example, in FIG. 16, the stack of test strips is loaded into the dispenser such that the "meter insertion end" of the test strips exits the dispenser first upon dispensing. (This is opposite to that shown in FIG. 2.) Further, the dispenser is configured with an additional "detent" position between the home and dispense positions described above, which is used to hold the test strip in place after the end of it has extended from the dispenser.

Figure 16:
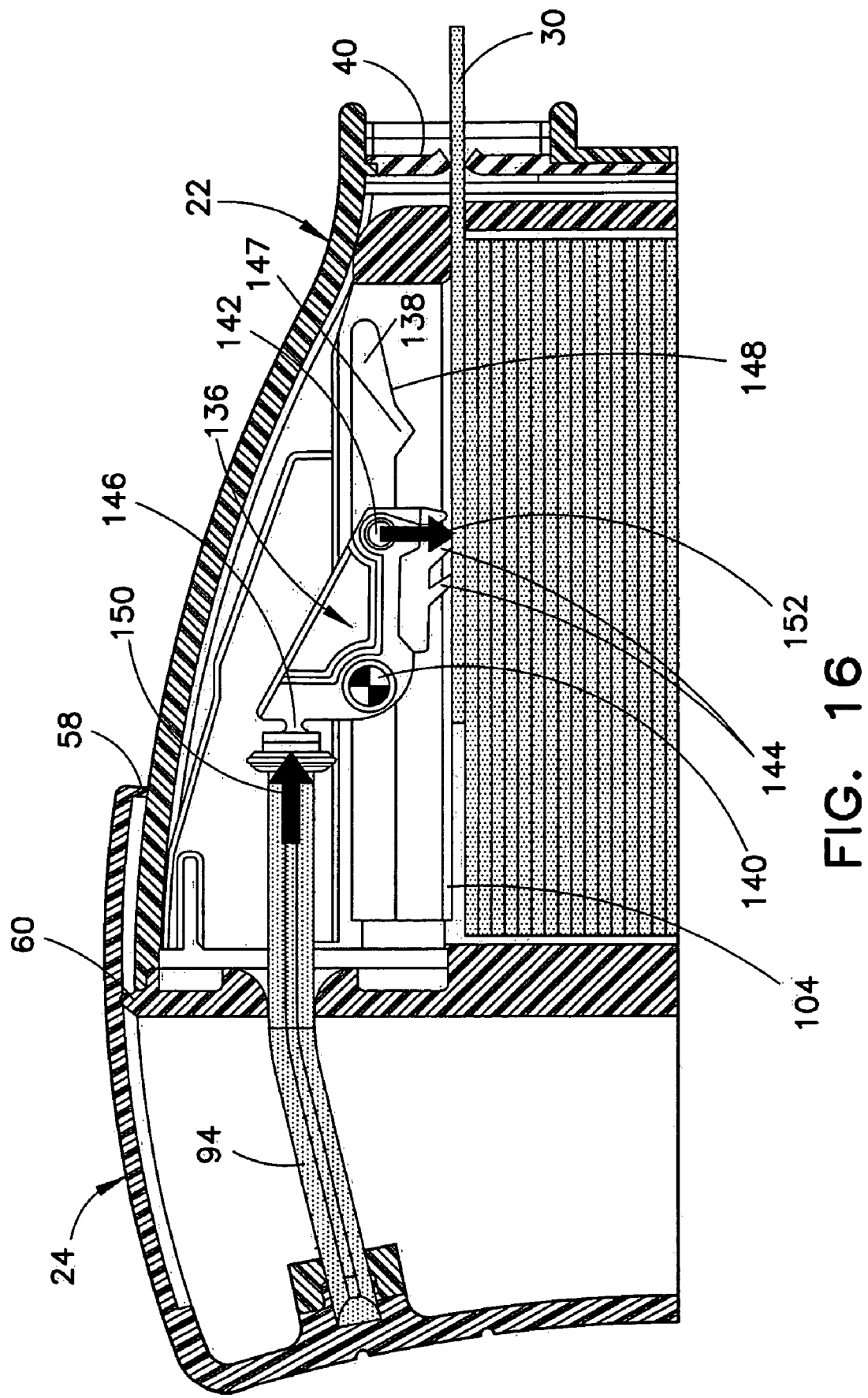
FIG. 16 is a side sectional view illustrating the movement of the dispenser of an embodiment of the present invention from the home position to an optional detent position.

With further reference to FIG. 16, groove 138 defines a notch or detent 147 such that posts 142 engage the detent 147 as the pusher head 136 slides to the right as the user squeezes the trigger and housing together. The detent 147 is positioned such that the posts 142 are guided into it as the dispenser is actuated. This happens after test strip 30 has passed partially through lip seal 42 and has a portion thereof extending from the dispenser as shown. The user experiences a tactile sensation when the forward movement of pusher head 136 stops as the posts 142 engage the detent 147. In this detent position, the fingers 144 remain frictionally engaged with the top test strip. The fingers 144 captively hold the test strip 30 such that the meter insertion end of the test strip 30 extends from the exit 32 of the dispenser.

Figure 17A:
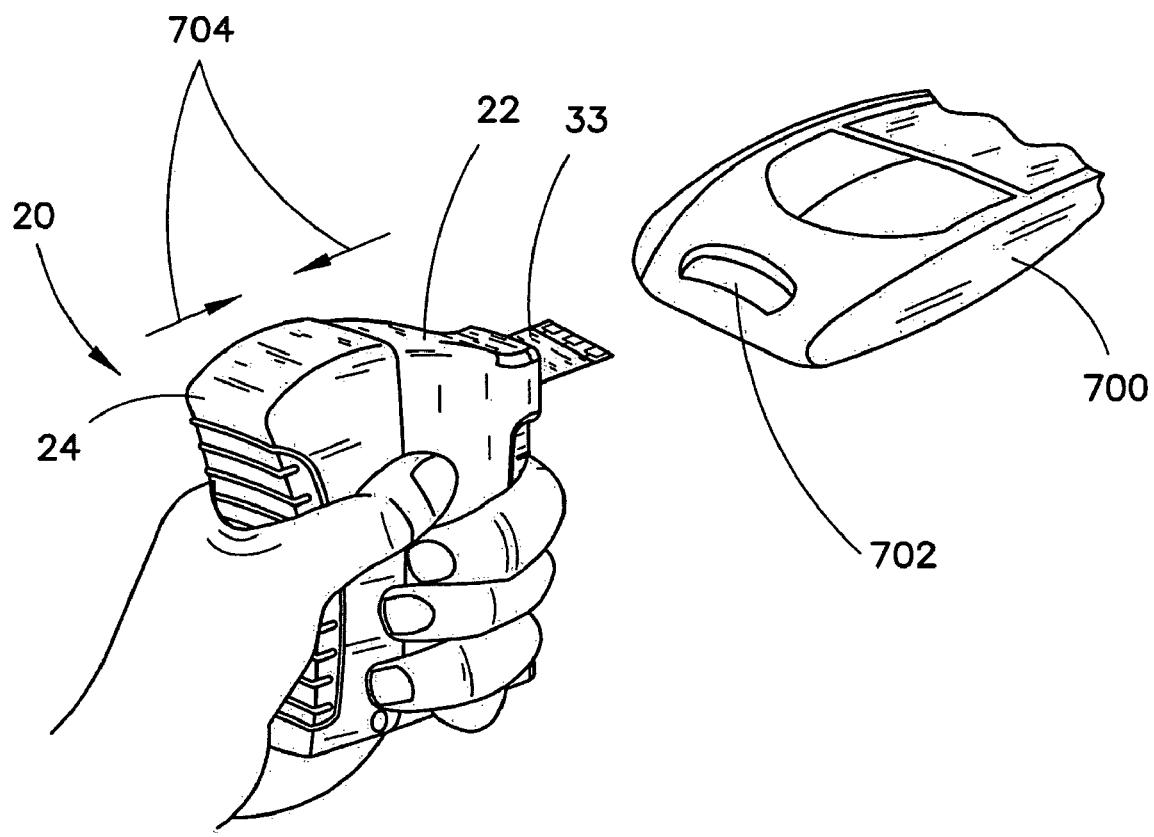
FIGS. 17a-17c are perspective views illustrating a method of using the article dispenser in accordance with the present invention with a meter that reads the articles that are dispensed.
Figure 17B:
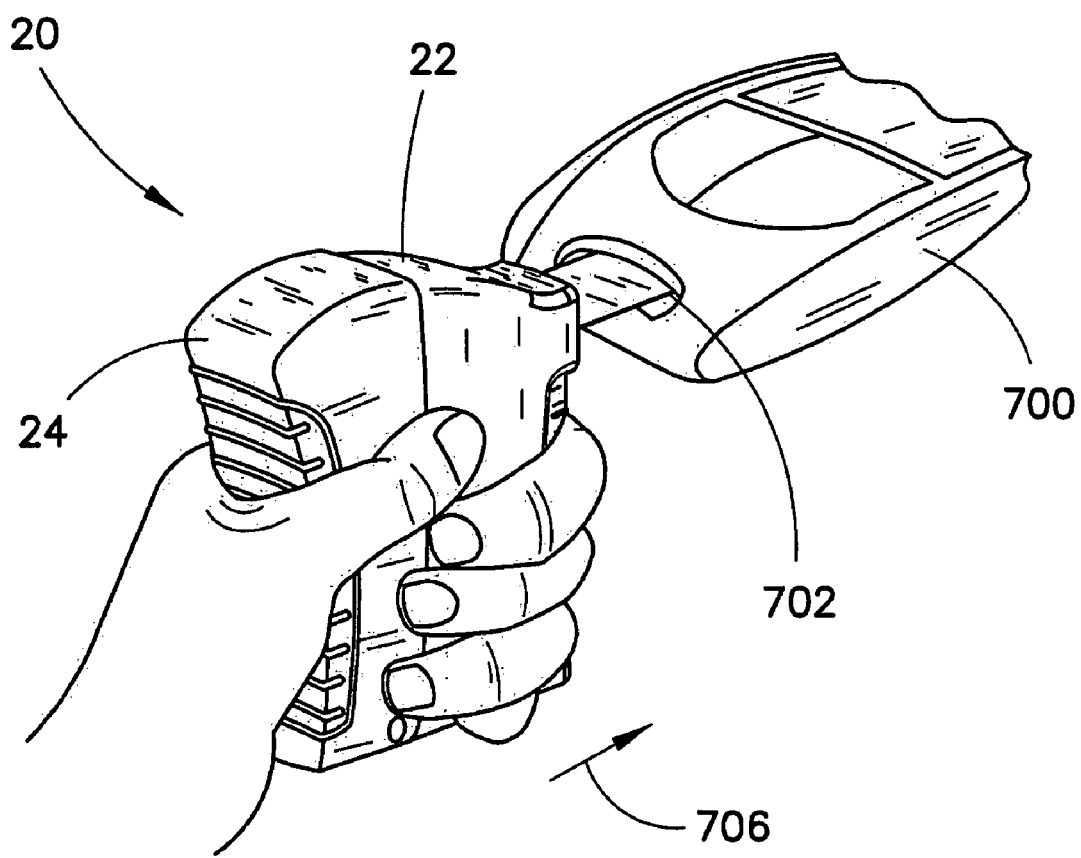
Figure 17C:
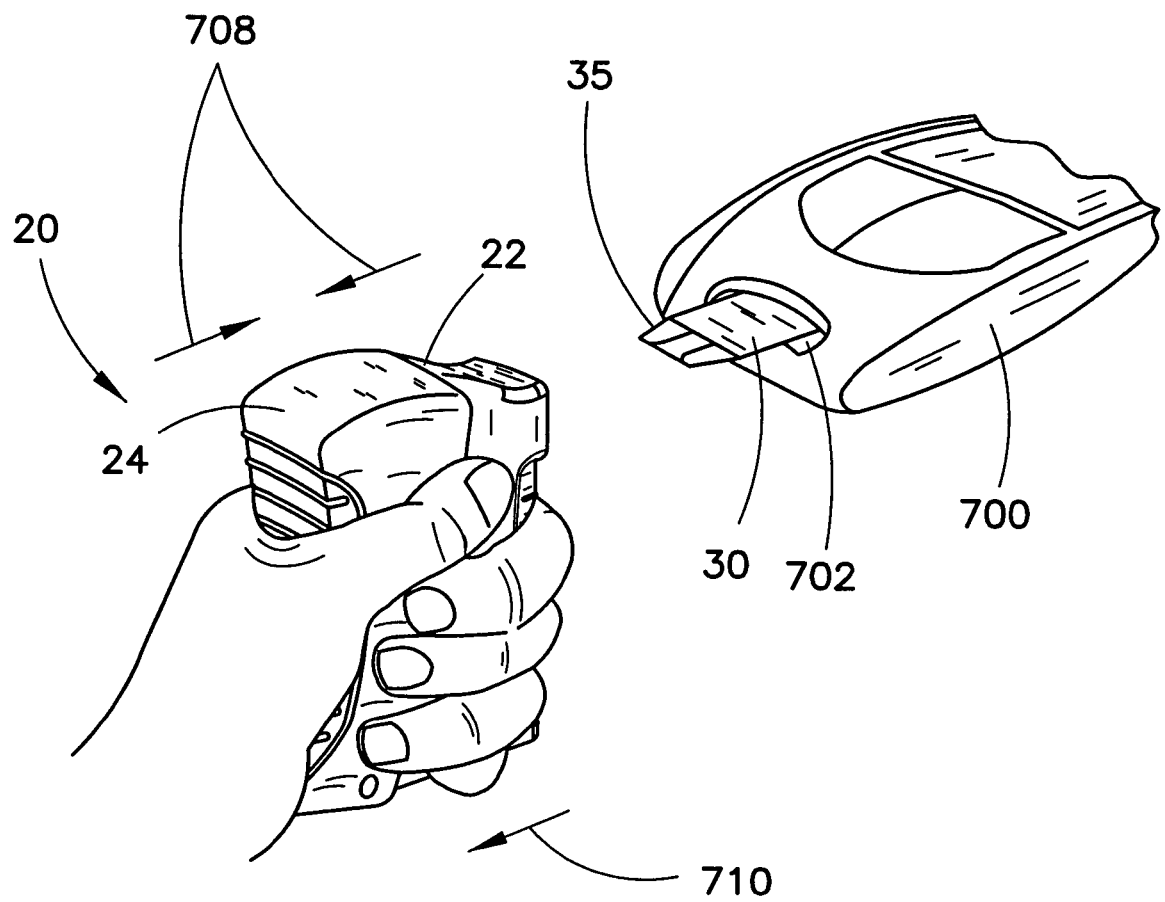

In this intermediate or detent position, the user can "dock" dispenser 20 to a test meter to receive the test strip 30. As shown in FIGS. 17a-17c, test meter 700 has an opening 702 to receive the meter insertion end 33 of test strip 30. In FIG. 17a, the user has squeezed trigger 24 and housing 22 together in the direction of arrows 704 to overcome the "passive lock" described above and has continued to squeeze trigger 24 and housing 22 together to the detent position. The detent position is signaled to the user through a tactile sensation produced by posts 142 engaging detent 147, at which point the forward movement of pusher head 136 stops. In this embodiment, the meter insertion end 33 of the test strip 30 extends from exit 32 of dispenser 20 and fingers 144 remain frictionally engaged with the test strip.

The user then aligns the end 33 of the test strip 30 with the opening 702 and moves the dispenser in the direction of arrow 706 in FIG. 17b so that the meter insertion end of the test strip is inserted into opening 702 of test meter 700. Preferably, the test meter 700 engages and captively holds the end of the test strip after it is inserted to the required depth.

At this point, the meter and dispenser are in close proximity. If the dispenser is configured with the optional RFID tag noted above, and meter 700 includes an RFID reader, the meter will download data from the RFID tag. Such data may include calibration data, expiration date and the like for the strips housed in dispenser 20. In many traditional test strip vials, this information is included in a memory chip that is packaged with the vial. The memory chip must be inserted into the meter by the user before using the strips in a given vial. The RFID tag disclosed herein can avoid the need for these memory chips and the need for the user to have to insert them into the meter.

After the dispenser and meter are "docked" as shown in FIG. 17b, the user then "releases" the test strip from the dispenser. With reference to FIG. 17c, this is done by fully squeezing the trigger 24 and the housing 22 together in the direction of arrows 708 to arrive at the "dispensed" position described above with respect to other embodiments. In the dispensed position, the fingers lift from the strip, thus releasing it. The dispenser can then be pulled away from the meter as shown by arrow 710 while leaving test strip 30 inserted in opening 702 of test meter 700, as shown in FIG. 17c. A dosing end 35 is thus protruding from the meter and is ready to receive a fluid sample.

While a preferred embodiment incorporating the principles of the present invention has been disclosed hereinabove, the present invention is not limited to the disclosed embodiments. Instead, as noted above, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A dispenser for flattened articles, comprising:
   a hollow body containing a stack of the articles and defining an opening through which the articles are dispensed;
   a pusher head slidably disposed in the body between a home position and a dispensed position, the pusher head having an engagement member for engaging the top surface of the top article of the stack when the pusher head is in the dispensed position, the pusher head being positioned above the top surface of the top article of the stack when the pusher head is in the home position; and
   a flexible arm member attached to the pusher head, the flexible arm member being actuable to move the pusher head into engagement with the top article in the stack and move the top article at least partially through the opening, wherein the flexible arm member flexes when actuated to rotate the pusher head from the home position to the dispensed position.

2. The dispenser of claim 1, wherein the flexible arm member is hingedly attached to the pusher head.

3. The dispenser of claim 1, wherein the flexible arm member is integrally formed with the pusher head.

4. The dispenser of claim 3, wherein the flexible arm member is hingedly attached to the pusher head.

5. The dispenser of claim 1, wherein the hollow body comprises a wall having an aperture through which the flexible arm member slides.

6. The dispenser of claim 5, wherein the flexible arm member includes a sealing member and the aperture includes a sealing surface, the sealing member engaging the sealing surface when the pusher head is positioned in the home position.

7. The dispenser of claim 6, wherein the sealing member comprises a flexible flange that circumscribes the flexible arm member, the flexible flange engaging a peripheral portion of the aperture when the pusher head is positioned in the home position.

8. The dispenser of claim 7, wherein the peripheral portion is flared or conically shaped.

9. The dispenser of claim 1, further comprising a housing in which the hollow body is positioned and a trigger pivotably connected to the housing, the flexible arm member being connected to the trigger, wherein pivoting movement of the trigger toward the housing causes the flexible arm member to move the pusher head into engagement with the top article in the stack and move the top article at least partially through the opening.

10. The dispenser of claim 9, wherein pivoting movement of the trigger away from the housing causes the flexible arm member to bias the pusher head away from the stack of articles.

11. The dispenser of claim 9, wherein the flexible arm member straightens as the housing and the body are pivoted toward one another.

12. The dispenser of claim 9, wherein the trigger defines a receptacle in which the housing at least partially nests as the housing and the trigger are pivoted together.

13. The dispenser of claim 9, wherein the body includes a resilient member that seats the body in the housing.

14. The dispenser of claim 9, wherein the housing further comprises an exit from which the articles are dispensed.

15. The dispenser of claim 14, wherein the exit comprises two resilient members biased together to form a lip seal.

16. The dispenser of claim 15, wherein the two resilient members are pushed apart as the articles pass between the two resilient members upon being dispensed.

17. The dispenser of claim 15, wherein the housing further comprises a lip seal cover covering the lip seal.

18. The dispenser of claim 17, wherein the lip seal cover comprises an opening through which the articles pass upon being dispensed.

19. The dispenser of claim 17, wherein the lip seal cover removably covers the lip seal.

20. The dispenser of claim 17, wherein the lip seal cover is hingedly attached to the housing.

21. The dispenser of claim 17, wherein the lip seal cover includes a biasing member contacting the lip seal and biasing the two resilient members together.

22. The dispenser of claim 21, wherein the biasing member comprises a leg wedged between the housing and the lip seal.

23. The dispenser of claim 22, wherein the leg comprises a pair of legs.

24. The dispenser of claim 23, wherein each of the legs is wedged between one of the resilient members and the housing.

25. The dispenser of claim 1, wherein the flattened articles comprise test strips.

26. A test strip dispenser, comprising:
a hollow body containing a stack of test strips and defining an opening through which the test strips are dispensed;
a pusher head positioned above the stack of test strips and slidably disposed in the body between a home position and a dispensed position, movement of the pusher head from the home position to the dispensed position defining a dispense stroke in which the pusher head frictionally engages a top surface of the top test strip and pushes the top test strip from the stack at least partially through the opening, movement of the pusher head from the dispensed position to the home position defining a return stroke; and
a guide assembly that biases the pusher head against the top surface of the top test strip of the stack during at least a portion of the dispense stroke, the guide assembly rotating the pusher head to engage the top surface of the top test strip during the dispense stroke, the guide assembly rotating the pusher head away from the top test strip as the dispense stroke ends.

27. The dispenser of claim 26, wherein the guide assembly comprises a groove defined by the body and at least one of a cam and a post extending from the pusher head and slidably received in the groove.

28. The dispenser of claim 27, wherein the pusher head includes the cam and the cam defines a pivot axis about which the pusher head pivots when moving toward and away from the stack of test strips.

29. The dispenser of claim 28, further comprising an actuable arm member hingedly attached to the pusher head, wherein actuating the arm member reciprocates the pusher head between the home and the dispensed positions and pivots the pusher head toward and away from the stack of test strips.

30. The dispenser of claim 27, wherein the groove comprises a detent.

31. The dispenser of claim 30, wherein at least one of the cam and post are slidably received in the detent.

32. The dispenser of claim 31, wherein the pusher head is biased against the top test strip when the at least one of the cam and post are slidably received in the detent.

33. The dispenser of claim 27, wherein the pusher head includes the post and the groove further comprises an inclined portion that engages the post as the dispense stroke ends and thereby moves the pusher head away from the top test strip, whereby the top test strip can be easily pulled from the dispenser.

34. The dispenser of claim 33, wherein the pusher head includes the cam and the pusher head pivots about the cam as the inclined portion engages the post.

35. The dispenser of claim 26, wherein the pusher head is spaced away from the stack of test strips when returning from the dispensed position to the home position.

36. The dispenser of claim 26, wherein the pusher head comprises a resilient finger extending downwardly therefrom, the finger engaging the top test strip during the dispense stroke.

37. The dispenser of claim 36, wherein the finger comprises a pair of fingers.

38. The dispenser of claim 26, wherein the hollow body is formed from a moisture absorbing material.

39. A dispenser for flattened articles, comprising:
a housing containing a stack of the articles and defining an opening through which the articles are dispensed;

a flexible seal disposed in the opening, the flexible seal comprising two resilient members for sealing the opening, the article passing between the two resilient members upon being dispensed; and a biasing member positioned adjacent the flexible seal, the biasing member configured to contact and squeeze the two resilient members together.

40. The dispenser of claim 39, further comprising a cap covering the flexible seal.

41. The dispenser of claim 40, wherein the cap comprises an opening through which the articles pass upon being dispensed.

42. The dispenser of claim 40, wherein the cap is removably attached to the housing.

43. The dispenser of claim 40, wherein the cap is integrally formed with the biasing member.

44. The dispenser of claim 40, wherein the cap is integrally formed with the housing.

45. The dispenser of claim 39, wherein the biasing member comprises a leg wedged between the housing and the flexible seal.

46. The dispenser of claim 45, wherein the leg comprises a pair of legs.

47. The dispenser of claim 46, wherein each of the legs is wedged between one of the resilient members and the housing.

48. The dispenser of claim 39, wherein the two resilient members are pushed apart as the articles pass between the two resilient members upon being dispensed.

49. The dispenser of claim 39, wherein the flexible seal comprises a lip seal.

50. The dispenser of claim 39, wherein ends of the resilient members overlap.

51. The dispenser of claim 39, wherein the flattened articles comprise test strips.

52. A dispenser for flattened articles, comprising:

a housing containing a stack of the articles and defining an opening through which the articles are dispensed; and a flexible seal disposed in the opening, the flexible seal including two resilient first walls, each of the first walls having an outer surface and an inner surface, the inner surfaces each having a convexly curved profile, the curved profile of each of the inner surfaces positioned adjacent one another for biasing the first walls together to seal the opening, the article passing between the two resilient first walls upon being dispensed, the flexible seal including two second walls, each of the second walls extending between the housing and one of the first walls.

53. The dispenser of claim 52, further comprising a cap covering the flexible seal.

54. The dispenser of claim 53, wherein the cap comprises an opening through which the articles pass upon being dispensed.

55. The dispenser of claim 53, wherein the cap is removably attached to the housing.

56. The dispenser of claim 53, wherein the cap is hingedly attached to the housing.

57. The dispenser of claim 53, wherein the cap is integrally formed with the housing.

58. The dispenser of claim 52, wherein the flattened articles comprise test strips.

* * * * *